United States Patent [19]

Krapcho

[11] 4,311,697
[45] Jan. 19, 1982

[54] DERIVATIVES OF MERCAPTOACYL PROLINES AND PIPECOLIC ACIDS

[75] Inventor: John Krapcho, Somerset, N.J.

[73] Assignee: E. R. Squibb & Sons, Inc., Princeton, N.J.

[21] Appl. No.: 99,164

[22] Filed: Nov. 30, 1979

Related U.S. Application Data

[63] Continuation-in-part of Ser. No. 972,314, Dec. 22, 1978, abandoned.

[51] Int. Cl.³ .................. A61K 31/40; A61K 31/445; C07D 207/16; C07D 211/34
[52] U.S. Cl. .................. 424/240; 260/326.2; 260/326.25; 260/326.35; 260/326.36; 260/326.42; 260/326.43; 260/326.47; 546/15; 546/19; 546/187; 546/188; 546/193; 546/212; 546/214; 546/242; 546/256; 546/280; 546/281; 424/246; 424/250; 424/251; 424/263; 424/267; 424/274
[58] Field of Search ........... 260/326.25, 326.2, 326.42, 260/326.43, 326.47, 326.35, 326.36; 546/193, 187, 281, 188, 212, 280, 214, 15, 19, 242, 256; 424/274, 250, 240, 267, 251, 246, 263

[56] References Cited

U.S. PATENT DOCUMENTS

| | | | |
|---|---|---|---|
| 4,046,889 | 9/1977 | Ondetti et al. | 260/326.2 |
| 4,105,776 | 8/1978 | Ondetti et al. | 260/326.2 |
| 4,116,962 | 9/1978 | Ondetti et al. | 424/274 |
| 4,154,840 | 5/1979 | Ondetti et al. | 424/267 |
| 4,154,935 | 5/1979 | Ondetti et al. | 424/274 |
| 4,198,515 | 4/1980 | Ondetti et al. | 260/326.2 |

Primary Examiner—Alton D. Rollins
Attorney, Agent, or Firm—Lawrence S. Levinson; Stephen B. Davis

[57] ABSTRACT

This invention is directed to compounds of the formula

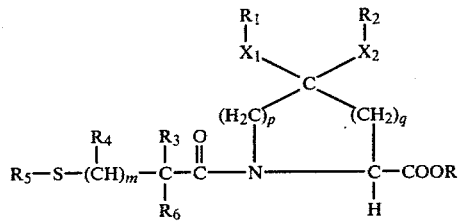

and various intermediates therefore. The final products possess useful hypotensive activity.

30 Claims, No Drawings

DERIVATIVES OF MERCAPTOACYL PROLINES AND PIPECOLIC ACIDS

RELATED APPLICATIONS

This application is a continuation-in-part of U.S. Ser. No. 972,314 filed Dec. 22, 1978, now abandoned.

BACKGROUND OF THE INVENTION

Mercaptoacyl derivatives of proline and pipecolic acid are disclosed as useful antihypertension agents due to their angiotensin converting enzyme inhibition activity in U.S. Pat. No. 4,105,776 of Ondetti et al.

Mercaptoacyl derivatives of proline and pipecolic acid wherein the acyl sidechain can be substituted by an alkyl or trifluoromethyl group and the ring can be substituted with one or more halogens are also useful as angiotensin converting enzyme inhibitors as note Ondetti et al. U.S. Pat. No. 4,154,935.

Mercaptoacyl derivatives of proline and pipecolic acid wherein the acyl sidechain can be substituted with a lower alkylthio group are also disclosed as angiotensin converting enzyme inhibitors by Ondetti et al. in U.S. Pat. No. 4,116,962.

Mercaptoacyl derivatives of proline wherein the ring can be substituted with an ether or thioether substituent are disclosed as useful antihypertension agents due to their angiotensin converting enzyme inhibition activity in copending application Ser. No. 52,691 filed July 2, 1979 of Ondetti and Krapcho, abandoned.

SUMMARY OF THE INVENTION

This invention relates to new derivatives of mercaptoacyl prolines and pipecolic acids of formula I and salts thereof

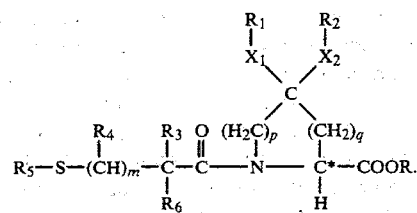

R and $R_6$ are independently selected from hydrogen and lower alkyl provided that $R_6$ is lower alkyl only if $R_3$ is also lower alkyl.

$R_3$ and $R_4$ are independently selected from hydrogen, lower alkyl, lower alkylthio, $-(CH_2)_n-SH$, and halo substituted lower alkyl.

$X_1$, $X_2$ and $X_3$ are independently selected from oxygen and sulfur.

$R_1$ and $R_2$ are independently selected from lower alkyl, lower alkenyl, lower alkynyl, cycloalkyl, halo substituted lower alkyl, hydroxy substituted lower alkyl,

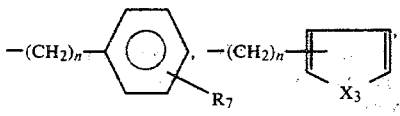

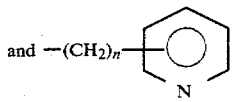

or $R_1$ and $R_2$ join in a polymethylene chain to complete an unsubstituted or substituted 5- or 6-membered ring.

When $R_1$ and $R_2$ are joined together in a polymethylene chain of 2 or 3 carbons, these cyclic ketal and thioketals can be represented as follows:

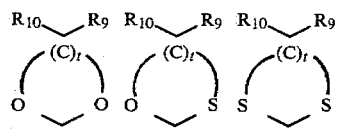

wherein t is 2 or 3 and $R_9$ and $R_{10}$ are both hydrogen, both lower alkyl, or one is hydrogen and the other is lower alkyl, halo substituted lower alkyl, hydroxy substituted lower alkyl,

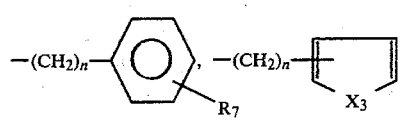

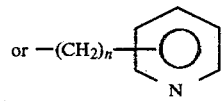

Preferably, only one carbon of the polymethylene chain will be substituted.

$R_7$ is hydrogen, lower alkyl of 1 to 4 carbons, especially methyl, lower alkoxy of 1 to 4 carbons, especially methoxy, lower alkythio of 1 to 4 carbons, especially methylthio, chloro, bromo, fluoro, trifluoromethyl, or hydroxy.

$R_5$ is hydrogen, a hydrolyzably removable protecting group, a chemically removable protecting group, or when $R_3$ and $R_4$ are other than $-(CH_2)_n-SH$ a sulfide of the formula

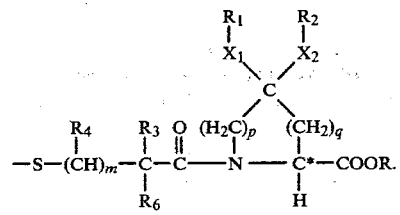

m is zero, one, or two.

n is one, two or three.

p and q are each one or two provided that both are not two.

The asterisk in the above formula indicates a center of asymmetry in the ring. In the case of proline, i.e., p and q are both one, this center is in the L-configuration. In the case of pipecolic acid, i.e., one of p and q is two, this center is in the D, L or L-configuration.

Asymmetric centers can also be present in the mercaptoacyl sidechain depending upon the definition of $R_3$, $R_4$ and $R_6$. Another assymmetric center may also be present in the ring when $X_1$-$R_1$ and $X_2$-$R_2$ are different. The products can accordingly exist in stereoisomeric forms or as racemic mixtures thereof. All of these are within the scope of the invention. The synthesis described below can utilize the racemate or one of the enantiomers as starting materials. When the racemic starting material is used in the synthesis procedure, the stereoisomers obtained in final product can be separated by conventional chromatographic or fractional crystallization methods. Preferably, if there is an asymmetric center in the mercaptoacyl sidechain, it is in the D-configuration.

DETAILED DESCRIPTION OF THE INVENTION

This invention in its broadest aspect relates to the mercaptoacyl derivatives of proline and pipecolic acid having formula I above and to salts thereof, to compositions containing such compounds and to the method for using such compounds as anti-hypertensive agents. This invention is also directed to certain novel intermediates useful in the preparation of compounds of formula I.

The term lower alkyl as used in defining the symbols R, $R_1$, $R_2$, $R_3$, $R_4$, and $R_6$ are straight or branched chain hydrocarbon radicals having up to seven carbons, for example, methyl, ethyl, propyl, isopropyl, butyl, isobutyl, t-butyl, pentyl, isopentyl, etc. The preferred lower alkyl groups are up to four carbons with methyl and ethyl being most preferred. Similarly, the terms lower alkoxy and lower alkylthio refer to such lower alkyl groups attached to an oxygen or sulfur.

The term cycloalkyl refers to saturated rings of 3 to 7 carbon atoms with cyclohexyl being most preferred.

The term halo substituted lower alkyl refers to such lower alkyl groups described above in which one or more hydrogens have been replaced by chloro, bromo or fluoro groups such as trifluoromethyl, pentafluoroethyl, 2,2,2-trichloroethyl, chloromethyl, bromomethyl, etc.

The term hydroxy substituted lower alkyl refers to such lower alkyl groups described above in which one hydrogen has been replaced by a hydroxy group such as hydroxymethyl, 2-hydroxyethyl, etc.

The term lower alkenyl as used in defining the symbols $R_1$ and $R_2$ are mono-saturated straight or branched chain hydrocarbon groups of from 2 to 7 carbons such as ethenyl, propenyl, isopropenyl, butenyl, and the like. The lower alkynyl groups are straight or branched chain hydrocarbon groups of from 2 to 7 carbons having one triple bond, e.g., propargyl. The preferred lower alkenyl groups are from 2 to 5 carbons and the preferred lower alkynyl groups are from 2 to 4 carbon atoms.

The term hydrolyzably removable protecting group employed in defining $R_5$ refers to a group that can be removed by conventional hydrolysis or ammonolysis. Acyl groups of the formula

are suitable for this purpose wherein $R_8$ can be lower alkyl of 1 to 7 carbons, lower alkyl substituted with one or more chloro, bromo or fluoro groups, $—(CH_2)_r—$cycloalkyl, an aryl group such as

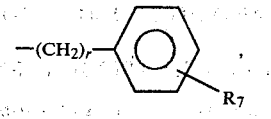

a hetero group such as

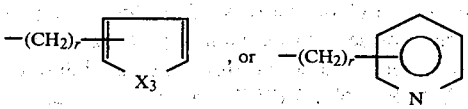

wherein r is zero, one, two or three, and $R_7$ and $X_3$ are as defined above. Preferred groups are the lower alkanoyl groups having up to four carbons, especially acetyl, and benzoyl.

The term chemically removable protecting group employed in defining $R_5$ refers to groups such as p-methoxybenzyl, p-methoxybenzyloxycarbonyl, trityl, t-butoxycarbonyl, etc. These groups can be removed after the completion of the acylation reaction by various means depending upon the definition of $X_1—R_1$ and $X_2—R_2$ such as by treatment with trifluoroacetic acid and anisole, sodium and liquid ammonia, or mercuric trifluoroacetate.

Preferred compounds of formula I are the L-proline containing derivative, i.e., p and q are both one, and R is hydrogen.

With respect to the mercaptoacyl sidechain, preferred as final products are those compounds wherein $R_5$ is hydrogen; m is zero or one; $R_4$ is hydrogen; and $R_3$ and $R_6$ are both lower alkyl of 1 to 4 carbons, especially both methyl, or $R_6$ is hydrogen and $R_3$ is hydrogen, lower alkyl of 1 to 4 carbons, especially methyl, trifluoromethyl, methylthio, or mercaptomethyl. Also preferred as both intermediates and final products are the above sidechains wherein $R_5$ is lower alkanoyl or 1 to 4 carbons, especially acetyl, or benzoyl.

Especially preferred as final products are the compounds of formula I having the mercaptoacyl sidechain wherein $R_5$ is hydrogen; m is one; $R_4$ and $R_6$ are hydrogen; $R_3$ is methyl; and the asymmetric carbon atom to which $R_3$ is attached is in the D-configuration.

Preferred compounds with respect to the substituents on the proline ring are those wherein $R_1$ and $R_2$ are independently selected from lower alkyl of 1 to 4 carbons, especially methyl or ethyl;

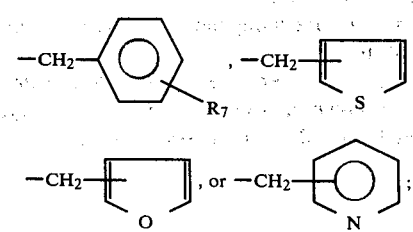

and $R_7$ is hydrogen, methyl, methoxy, methylthio, Cl, Br, F, trifluoromethyl, or hydroxy; or $X_1—R_1$ and $X_2—R_2$ join to form

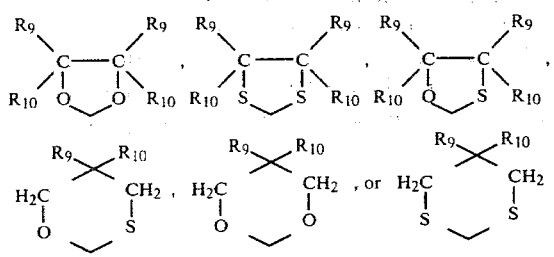

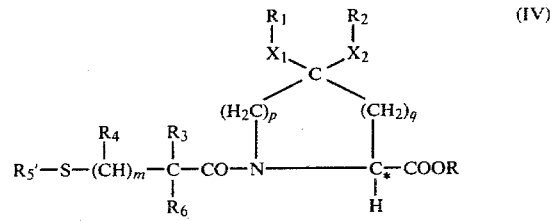

wherein $R_9$ and $R_{10}$ are both hydrogen or both lower alkyl of 1 to 4 carbons, especially both hydrogen or both methyl, or $R_9$ is hydrogen and $R_{10}$ is lower alkyl of 1 to 4 carbons, especially methyl, hydroxy substituted lower alkyl of 1 to 4 carbons, especially hydroxymethyl, or halo substituted lower alkyl, especially trifluoromethyl.

Most preferred compounds with respect to the substituents on the proline ring are those wherein $X_1$ and $X_2$ are the same especially those wherein $X_1$—$R_1$ and $X_2$—$R_2$ are both methoxy or both ethoxy or $X_1$—$R_1$ and $X_2$—$R_2$ join together to form

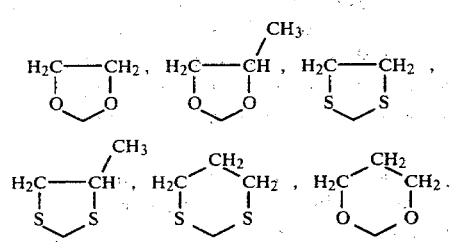

The compounds of formula I are obtained by coupling the substituted proline or pipecolic acid of the formula

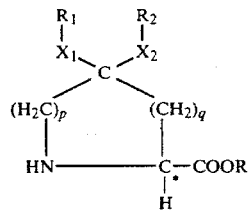

with an acid or its chemical equivalent of the formula

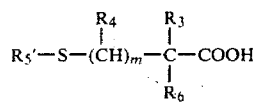

wherein $R_5'$ is hydrogen, a hydrolyzably or chemically removable protecting group to yield the product of the formula This reaction can be effected in the presence of a coupling agent such as dicyclohexylcarbodiimide or the like, or the acid can be activated by formation of its mixed anhydride, symmetrical anhydride, acid halide, active ester or use of Woodward reagent K, N-ethoxycarbonyl-2-ethoxy-1,2-dihydroquinoline or the like. For a review of the methods of acylation, see Methoden der Organishchen Chemie (Houben-Weyl), Vol. XV, part II, page 1 et seq. (1974). Preferably, the acid halide, especially the acid chloride, of formula III is reacted with the acid of formula II.

If the proline or pipecolic acid of formula II is reacted in the ester form the resulting ester product of formula IV, i.e., R is alkyl, can be converted to the free acid, i.e., R is hydrogen, by conventional means. For example, if R is ethyl this ester protecting group can be removed by saponification.

The product of formula IV is preferably isolated and purified by crystallization, e.g., by forming the dicyclohexylamine salt and then converting the salt to the free acid form by treatment with an aqueous solution of an acid, such as potassium acid sulfate.

The product of formula IV bearing the acyl group $R_8$—CO— can be converted to the products of formula I wherein $R_5$ is hydrogen by conventional hydrolysis or by ammonolysis.

The products of formula I wherein $R_3$ and $R_4$ are other than —(CH$_2$)$_n$—SH and $R_5$ is

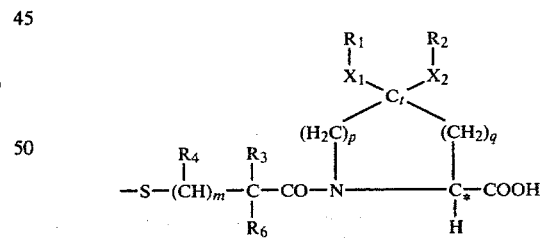

are obtained by directly oxidizing with iodine a product of formula I wherein $R_5$ is hydrogen.

The esters of formula I wherein R is lower alkyl can be obtained from the carboxylic acid compounds, i.e., wherein R is hydrogen, by conventional esterification procedures, e.g., by esterification with a diazoalkane such as diazomethane, a 1-alkyl-3-p-tolyltriazene, such as 1-n-butyl-3-p-tolyltriazene, or the like.

The disubstituted prolines or pipecolic acids of formula II wherein $X_1$—$R_1$ and $X_2$—$R_2$ are the same, can be obtained by reacting an N-protected keto compound of the formula

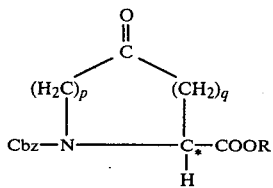

wherein Cbz represents carbobenzyloxy with an alcohol or thiol having the formula

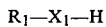 (VI)

in the presence of an orthoformate or thioformate of the formula $HC(X_1-R_1)_3$ and an acid such as concentrated sulfuric acid or p-toluenesulfonic acid. This reaction can be effected in an inert organic solvent such as benzene, acetic acid, ether, cyclohexane or the like, preferably with heating, e.g., at about reflux temperature. See Buehler et al., *Survey of Organic Syntheses* (Wiley & Sons, 1977) Vol. 1, pages 516–519. The product of this reaction is the N-protected intermediate of the formula

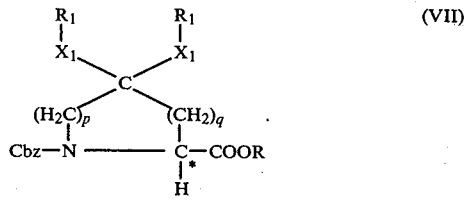 (VII)

The N-protected intermediate of formula VII can be treated with a molar equivalent of an alcohol or thiol of the formula

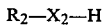 (VIII)

according to the conditions described above to yield the intermediate

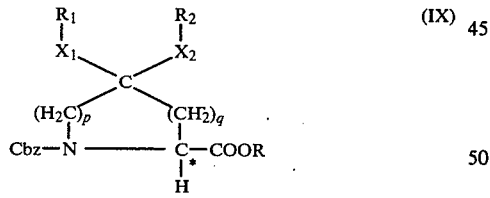 (IX)

By employing a molar excess of the alcohol or thiol of formula VIII one obtains the intermediate

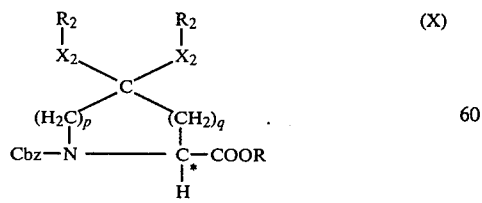 (X)

The N-protecting group can then be removed by conventional procedures, for example, when $X_1$ and $X_2$ are both oxygen by hydrogenolysis in the presence of palladium carbon catalyst or when either or both $X_1$ and $X_2$ are sulfur by treatment with HBr and acetic acid to yield the disubstituted compounds of formula II.

Similarly, the spiro compounds of formula II (i.e., $R_1$ and $R_2$ are joined together in a polymethylene chain) can be obtained by reacting the keto compound of formula V with the alcohol or thiol of the formula

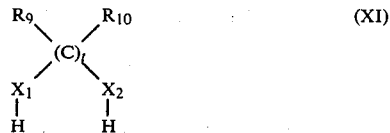 (XI)

wherein $R_9$, $R_{10}$, and t are defined above in the presence of an acid such as p-toluenesulfonic acid, to yield the intermediate (XII)

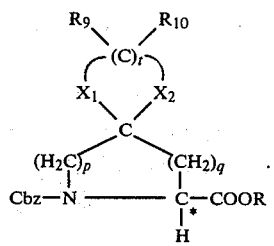

Alternatively, the disubstituted compound of formula VII can be treated directly with a molar excess of the alcohol or thiol of formula XI to yield the intermediate of formula XII. This procedure is particularly useful when $R_9$ and $R_{10}$ are either or both other than hydrogen.

As described above, the N-protecting group can then be removed to yield the spiro compounds of formula II.

As an alternative procedure, the introduction of the $X_1$-$R_1$ and $X_2$-$R_2$ groups can be effected later in the sequence. According to this modification, the protected keto compound of formula V is treated to remove the protecting group, e.g., with hydrogen bromide, resulting in an intermediate having the formula

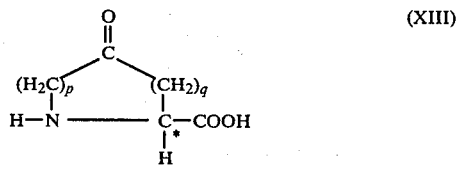 (XIII)

which is then acylated with the acid, preferably the acid halide, of formula III to yield the compound of the formula

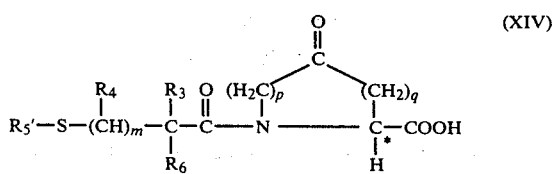 (XIV)

The groups $X_1$-$R_1$ and $X_2$-$R_2$ or the spiro group

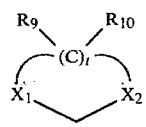

can then be introduced at this point by the procedures described above to yield the product of formula IV.

Reference is also made to the following publications for additional illustrative methodology for producing starting materials and intermediates: U.S. Pat. Nos. 4,046,889, 4,105,776, 4,154,935 and 4,116,962; Can. J. Biochem. & Physiol. 37, 584 (1959); J.A.C.S. 79, 189 (1957); J. Med. Chem. 21, 445 (1978); Aus. J. Chem. 20, 1493–1509 (1967); Buehler et al., Survey of Organic Syntheses (Wiley & Sons, 1977), Vol. 1, pages 516–519, Vol. 2 pages 461–470; Chem. Pharm. Bull., Tokyo 26, 2209 and 2217 (1978); Can. J. Chem. 47, 860 (1969); J. Amer. Chem. Soc., 80, 6350 (1958); Harrison et al., Compendium of Organic Synthetic Methods, (Wiley-Interscience, New York, 1971), pages 449–456; J. Amer. Chem. Soc., 79, 192 (1956); Bull. Soc. Chem., 1965(8) pages 2253–2259; J. Org. Chem. 25, p. 521–530 (1960).

The procedures illustrated therein can be utilized as general methods for the synthesis of compounds and separation of isomers which can be utilized in the invention described in this application. Additional illustrative details are found in the examples which serve as models for the preparation of other members of the group.

The compounds of this invention form basic salts with a variety of inorganic or organic bases. The salt forming ion derived from such bases can be metal ions, e.g., aluminum, alkali metal ions, such as sodium or potassium, alkaline earth metal ions such as calcium or magnesium, or an amine salt ion, of which a number are known for this purpose, for example aralkylamines like, dibenzylamine, N,N-dibenzylethylenediamine, lower alkylamines like methylamine, t-butylamine, procaine, lower alkylpiperidines like N-ethylpiperidine, cycloalkylamines, like cyclohexylamine or dicyclohexylamine, 1-adamantanamine, benzathine, or salts derived from amino acids like arginine, lysine or the like. The physiologically acceptable salts like the sodium or potassium salts can be used medicinally as described below and are preferred. These and other salts which are not necessarily physiologically acceptable are useful in isolating or purifying a product acceptable for the purposes described below, as illustrated with the dicyclohexylamine salt in the examples. The salts are produced by reacting the acid form of the compound with a equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compound of formula I wherein R₅ is hydrogen,

or the disulfide type substituent, especially wherein R₅ is hydrogen, are useful as hypotensive agents. They inhibit the conversion of the decapeptide angiotensin I to angiotensin II and, therefore, are useful in relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one, or a combination of compounds of formula I angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises (for a 70 kg. mammal) a total daily dosage of about 30 to 600 mg., preferably about 30 to 300 mg., of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorothiazide, flumethiazide, hydroglumethiazide, benzdroflumethiazide, methchlothiazide, trichlormethiazide, polythiazide or benzthiazide, as well as ethacrynic acid, ticrynafen, chlorthalidone, furosemide, musolimine, bumetanide, triamterene, amiloride and spironolactone, and salts of such compounds.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative process details are set forth in the following examples for the various reactions. These examples are preferred embodiments and also serve as models for the preparation of other compounds of this invention. The temperatures are given in degrees on the centigrade scale.

EXAMPLE 1

[7(S),8S]-7-[3-(Acetylthio)-2-methyl-1-oxopropyl]-1,4-dioxo-7-azaspiro[4.4]nonane-8-carboxylic acid (a) N-Carbobenzyloxy-4-hydroxy-L-proline 26.5 g. (0.20 mole) of 4-hydroxy-L-proline and 32.8 ml. (0.23 mole) of benzyl chloroformate are reacted in 200 ml. of water and 100 ml. of acetone in the presence of 20 g. (0.02 mole) of potassium bicarbonate and 69.2 g. (0.50 mole) of potassium carbonate and worked up with 90 ml. of concentrated hydrochloric acid as described in Can. J. Biochem. & Physiol. 37, 584 (1959) to obtain N-carbobenzyloxy-4-hydroxy-L-proline. This product is reacted with cyclohexylamine to form the cyclohexylamine salt yield 69 g., m.p. 193°–195°. The salt (34 g.) is neutralized with N-hydrochloric acid to obtain 27 g. of free acid as a colorless glass $[\alpha]_D^{26} -70°$, (c, 1% in chloroform).

(b) N-carbobenzyloxy-4-keto-L-proline 21.5 g. (0.81 mole) of N-carbobenzyloxy-4-hydroxy-L-proline is oxidized in 1.2 liters of acetone with 83 ml. of 8 N chromic acid in sulfuric acid as described in J.A.C.S. 79, 189 (1957). In order to facilitate the subsequent filtration of chromium salts, 30 g. of Celite (diatomaceous earth) is added to the acetone solution before introduction of the oxidizing agent. An air stirrer is employed. The reaction mixture is filtered and the acetone filtrate is concentrated to approximately 300 ml. before diluting with 1 liter of chloroform. The solution is washed with 300 ml. of saturated sodium chloride (four times), dried (MgSO$_4$), filtered and the solvent evaporated to give N-carbobenzyloxy-4-keto-L-proline (22.8 g.) which is crystallized from ether (50 ml.)-hexane (150 ml.) to obtain 17.2 g. (81%) of product, m.p. 99°–101°, $[\alpha]_D^{26} +17°$ (c, 1% in chloroform).

(c) N-Carbobenzyloxy-4,4-ethylenedioxy-L-proline

A stirred mixture of 12.8 g. (0.049 mole) of N-carbobenzyloxy-4-keto-L-proline, 53 ml. (0.095 mole) of ethylene glycol, and 0.35 g. of p-toluenesulfonic acid.-H$_2$O in 1.31 l. of benzene is heated and the resulting solution is refluxed for 7 hours (water formed is collected in a Dean-Stark apparatus). After standing overnight at room temperature, the lower glycol layer is separated and the benzene solution is washed with 150 ml. of saturated sodium chloride, dried (MgSO$_4$), and the solvent evaporated to give 14.6 g. of N-carbobenzyloxy-4,4-ethylenedioxy-L-proline as a syrupy residue. The latter is dissolved in 60 ml. of ethanol, filtered, treated with 5 g. of cyclohexylamine, and diluted with ether. On seeding and rubbing, the crystalline cyclohexylamine salt separates; weight after cooling overnight, 9.0 g., m.p. 179°–180° (s. 173°). The material is recrystallized from acetonitrile, m.p. 182°–184° (s. 179°), $[\alpha]_D^{26} -21°$ (c, 1% in EtOH).

The cyclohexylamine salt (8.4 g.) is suspended in 40 ml. of ethyl acetate, stirred, cooled, and treated with 40 ml. of 1 N hydrochloric acid. The layers are separated, the aqueous phase extracted with additional ethyl acetate (3×40 ml.), the combined organic layers are dried (MgSO$_4$), and the solvent evaporated, finally at 0.2 mm. The syrupy residue which begins to crystallize is rubbed under ether and the ether evaporated to give 6.4 g. (42%) of nearly colorless N-carbobenzyloxy-4,4-ethylenedioxy-L-proline, m.p. 101°–103° (s. 98°), $[\alpha]_D^{26} -34°$ (c, 1% in CHCl$_3$).

(d) 4,4-Ethylenedioxy-L-proline

A solution of 3.2 g. (0.0104 mole) of N-carbobenzyloxy-4,4-ethylenedioxy-L-proline in 100 ml. of methanol-water (2:1) is treated with 1 g. of 5% palladium-carbon and shaken on the Parr hydrogenator for 6 hours. The catalyst is filtered off under nitrogen, washed with methanol, and the combined filtrates evaporated, finally at 0.1–0.2 mm, to give 1.7 g. (94%) of colorless solid, 4,4-ethylenedioxy-L-proline; m.p. 245°–247° (dec.); $[\alpha]_D^{26} -32°$ (c,0.5% in 1:1 meOH—H$_2$O).

(e) [7(S),8S]-7-[3-(Acetylthio)-2-methyl-1-oxopropyl]-1,4-dioxo-7-azaspiro[4.4]nonane-8-carboxylic acid A stirred solution of 3.2 g. of 4,4-ethylenedioxy-L-proline (0.0185 mole) in 50 ml. of water is cooled to 5° and treated portionwise with solid sodium carbonate to pH 8.5. Then while continuing stirring and cooling, a solution of 3.7 g. (0.020 mol.) of D-3-acetylthio-2-methylpropanoyl chloride in 5 ml. of ether is added portionwise while maintaining the pH at 8.5 with 25% sodium carbonate solution (about 14 ml.). After 1¼ hours, the solution is treated with 50 ml. of ethyl acetate, stirred, cooled, acidified carefully with hydrochloric acid (1:1) to pH 2.0, saturated with sodium chloride and the layers are separated. The aqueous phase is extracted with additional ethyl acetate (3×50 ml.), the combined organic layers are dried (MgSO$_4$) and the solvent evaporated finally at 0.2 mm. The solid residue is rubbed under ether and the evaporation repeated to obtain 5.9 g. (100%) of [7(S), 8S]-7-[3-(acetylthio)-2-methyl-1-oxopropyl]-1,4-dioxo-7-azaspiro[4.4]nonane-8-carboxylic acid; m.p. 108°–111°.

The product is converted to the dicyclohexylamine salt with 3.4 g. of dicyclohexylamine in 70 ml. of ethyl acetate. On seeding and rubbing, the crystalline salt precipitates and is recrystallized from 95 ml. of acetonitrile; yield 6.7 g., m.p. 187°–189° (s. 184°), $[\alpha]_D^{25} -59°$ (c, 1% in EtOH).

The dicyclohexylamine salt is converted to the free acid by suspending it in ethyl acetate and treating with 75 ml. of 10% potassium bisulfate and stirring until two layers are obtained. After separating, the aqueous phase is extracted with ethyl acetate (4×75 ml.), the organic layers are combined, dried (MgSO$_4$) and the solvent is evaporated to give 4.1 g. of colorless [7(S),8S]-7-[3-(acetylthio)-2-methyl-1-oxopropyl]-1,4-dioxo-7-azaspiro[4.4]nonane-8-carboxylic acid, m.p. 120°–122° (s. 117°) $[\alpha]_D^{25} -118°$ (c, 1% in EtOH).

EXAMPLE 2

[7(S)-8S]-7-(3-Mercapto-2-methyl-1-oxopropyl)-1,4-dioxo-7-azaspiro[4.4]nonane-8-carboxylic acid Argon is passed through a cold solution of 8.5 ml. of concentrated ammonium hydroxide in 20 ml. of water. 4.0 g. (0.013 mole) of [7(S),8S]-7-[3-(acetylthio)-2-methyl-1-oxopropyl]-1,4-dioxo-7-azaspiro-[4.4]nonane-8-carboxylic acid from Example 1e are then added and the mixture is stirred in an ice bath for a few minutes and then a room temperature under argon for two hours. The solution is treated with 30 ml. of ethyl acetate, cooled, stirred, and acidified with 16 ml. of of hydrochloric acid (1:1). The layers are separated, the aqueous phase is extracted with additional 30 ml. of ethyl acetate (twice), the ethyl acetate extracts are combined, dried (MgSO$_4$) and the solvent evaporated to give [7(S),8S]-7-(3-mercapto-2-methyl-1-oxopropyl)-1,4-dioxo-7-azaspiro[4.4]nonane-8-carboxylic acid as a solid residue. The product is rubbed under ether and the evaporation is repeated. The product is then triturated with 30 ml. of hexane, cooled for one hour, filtered under argon and dried in vacuo to give 2.7 g. of colorless solid [7(S),8S]-7-(3-mercapto-2-methyl-1-oxopropyl)-1,4-dioxo-7-azaspiro[4.4]nonane-8-carboxylic acid, m.p. 131°–133° (s. 125°), $[\alpha]_D^{25} -66°$ (c, 1% in EtOH).

EXAMPLE 3

(S)-1-[(3-Acetylthio)-2-methyl-1-oxopropyl]-4,4-dimethoxy-L-proline (a) N-Carbobenzyloxy-4,4-dimethoxy-L-proline, methyl ester A stirred solution of 7.8 g. (0.03 mole) of N-carbobenzyloxy-4-keto-L-proline from Example 1 in 60 ml. of methanol is treated with 96 ml. of trimethyl orthoformate, followed by 0.6 ml. of concentrated sulfuric acid and allowed to stand overnight at room temperature.

The pale yellow solution is stirred, treated with 1.5 g. of potassium carbonate, followed by 30 ml. of water and the bulk of the solvent is removed on a rotary evaporator to give a syrupy residue which is shaken with 30 ml. of water and 30 ml. of chloroform. After separating the layers the aqueous phase is extracted with additional chloroform (3×30 ml.) and the combined organic layers are washed with 45 ml. of saturated sodium chloride solution and dried (MgSO$_4$). Evaporation of the solvent yields 8.4 g. (88%) of N-carbobenzyloxy-4,4-dimethoxy-L-proline, methyl ester.

(b) N-Carbobenzyloxy-4,4-dimethoxy-L-proline

The ester (8.4 g., 0.026 mole) from part a is dissolved in 80 ml. of methanol, treated dropwise at −1° to 4° with 18 ml. (0.036 mole) of 2 N sodium hydroxide kept at 0° for one hour, and at room temperature overnight. After removing about one half of the solvent on a rotary evaporator, the solution is diluted with 150 ml. of water, washed with 100 ml. of ether (wash discarded), acidified while cooling with 63 ml. of 1:1 hydrochloric acid to pH 2, and extracted with ethyl acetate (4×750 ml.). The combined extracts are washed with 50 ml. of saturated sodium chloride solution, dried (MgSO$_4$), and the solvent evaporated to give 8.0 g. of a pale yellow viscous oil. The oil is dissolved in 35 ml. ethanol, treated with 3.0 g. of cyclohexylamine in 10 ml. of ethanol and diluted to 500 ml. with ether. On seeding and rubbing, the crystalline N-carbobenzyloxy-4,4-dimethoxy-L-proline cyclohexylamine salt separated; weight after cooling overnight, 7.0 g., m.p. 157°–159° (s, 151) $[\alpha]_D^{26} -34°$ (c, 1% in EtOH). This material is recrystallized from 100 ml. of acetonitrile to give the salt as a colorless solid, m.p. 158°–160° (s, 154°) $[\alpha]_D^{26} -33°$ (c, 1% in EtOH).

The N-carbobenzyloxy-4,4-dimethoxy-L-proline cyclohexylamine salt is suspended in 40 ml. of ethyl acetate, stirred and treated with 25 ml. of 1 N hydrochloric acid. When two clear layers are obtained they are separated, the aqueous phase is extracted with additional ethyl acetate (3×40 ml.), the combined organic layers are dried (MgSO$_4$), and the solvent evaporated, finally at 0.2 mm and 40° to yield 7.2 g. (70%) of N-carbobenzyloxy-4,4-dimethoxy-L-proline as a pale yellow viscous syrup.

(c) 4,4-Dimethoxy-L-proline

A solution of N-carbobenzyloxy-4,4-dimethoxy-L-proline (72 g., 0.022 mole) in 210 ml. of methanol-water (2:1) is treated with 2.3 g. of 5% palladium-carbon and shaken on a Parr hydrogenator for 6 hours. The catalyst is filtered off under nitrogen, washed with methanol, and the combined filtrates are evaporated, finally at 0.1–0.2 mm., to give a partly crystalline residue. This residue is taken up in 200 ml. of methanol and the evaporation repeated. When the solid is rubbed under ether (evaporation again repeated) there is obtained 3.6 g. (95%) of nearly colorless 4,4-dimethoxy-L-proline, m.p. 192°–194° (dec.); $[\alpha]_D^{26} -47°$ (c, 1% in MeOH).

A sample crystallized from methanol-ether is colorless and melts at 197°–198° (dec.); $[\alpha]_D^{26} -49°$ (c, 1% in MeOH).

(d) (S)-1-[3-(Acetylthio)-2-methyl-1-oxopropyl]-4,4-dimethoxy-L-proline

A stirred solution of 3.3 g. (0.019 mole) of 4,4-dimethoxy-L-proline in 50 ml. of water is cooled to 5° and brought to pH 8.5 by the addition of 25% sodium carbonate solution (w/v). Then while continuing stirring and cooling, a solution of 3.8 g. (0.021 mole) of D-3-acetylthio-2-methylpropanoyl chloride in 5 ml. of ether is added portionwise while maintaining the pH at 7.5–8.5 by dropwise addition of 25% sodium carbonate solution. When the pH has stabilized at 8.2–8.4 (after about 15 minutes), stirring and cooling is continued for a total of one hour. The solution is then washed with 50 ml. of ethyl acetate (wash discarded, layered over with 50 ml. of ethyl acetate, cooled, stirred, acidified carefully with 1:1 hydrochloric acid to pH 2.0, saturated with sodium chloride, and the layers separated. The aqueous phase is extracted with additional ethyl acetate (3×50 ml.), the combined organic layers are dried (MgSO$_4$), and the solvent evaporated, finally at 0.2 mm, to give 6.7 g. of syrupy product. This syrup is treated in 70 ml. of ethyl acetate with 3.9 g. of dicyclohexylamine to give 6.5 g. of colorless (S)-1-[3-(acetylthio)-2-methyl-1-oxopropyl]-4,4-dimethoxy-L-proline dicyclohexylamine salt in crops (3.1 g. and 3.4 g.), m.p. 158°–160° (s, 145°). $[\alpha]_D^{26} -71°$ (c, 1% in EtOH).

Following recrystallization from 20 ml. of hot ethyl acetate-60 ml. of hexane, the colorless solid salt weighs 6.0 g., m.p. 158°–166° (s, 155°), $[\alpha]_D^{25} -69°$ (c, 1% in EtOH).

The dicyclohexylamine salt is converted to the free acid by suspending 5.0 g. in 50 ml. of ethyl acetate, cooling and treating with 60 ml. of 10% potassium bisulfate solution to give 2 clear layers. After separating, the aqueous phase is extracted with ethyl acetate (3×50 ml.), the combined organic layers are dried (MgSO$_4$), and the solvent evaporated, finally at 0.1–0.2 mm. and 45° to give 4.1 g. (69%) of (S)-1-[3-(acetylthio)-2-methyl-1-oxopropyl]-4,4-dimethoxy-L-proline as a viscous, almost glass-like material $[\alpha]_D^{25} -112°$ (c, 1% in EtOH).

EXAMPLE 4

(S)-1-(3-Mercapto-2-methyl-1-oxopropyl)-4,4-dimethoxy-L-proline

Argon is passed through a cold solution of 8.5 ml. of concentrated ammonium hydroxide in 20 ml. of water for 0.25 hour. The latter is then added while cooling and under a blanket of argon to 4.1 g. (0.013 mole) of (S)-1-[3-(acetylthio)-2-methyl-1-oxopropyl]-4,4-dimethoxy-L-proline and the mixture is swirled in an icebath until a pale yellow solution is obtained (about 15 minutes). Stirring under argon is continued at room temperature for an additional 2 hours, then the solution is extracted with 30 ml. of ethyl acetate (this and subsequent operations are carried out as much as possible under an argon atmosphere). The aqueous layer is cooled, stirred, layered over with 30 ml. of ethyl acetate, and acidified portionwise with approximately 16 ml. of 1:1 hydrochloric acid. The layers are separated, the aqueous phase is extracted with additional ethyl acetate (3×30 ml.), the combined ethyl acetate layers are dried (MgSO₄), and the solvent evaporated to give 3.5 g. (100%) of (S)-1-(3-mercapto-2-methyl-1-oxopropyl)-4,4-dimethoxy-L-proline as a colorless, viscous syrup, $[\alpha]_D^{25}$ −72° (c, 1% in EtOH).

The latter (3.4 g.) is triturated with 20 ml. of ethyl acetate, rubbed, diluted with 30 ml. of hexane, and cooled to give a colorless solid, weight 2.6 g., m.p. 108°–110°, $[\alpha]_D^{25}$ −77° (c, 1% in EtOH).

EXAMPLE 5

(S)-1-[3-(Acetylthio)-2-methyl-1-oxopropyl]-4,4-diethoxy-L-proline (a) N-Carbobenzyloxy-4,4-diethoxy-L-proline, ethyl ester Following the procedure of Example 3 (a) but substituting triethyl orthoformate for the trimethyl orthoformate and ethanol for the methanol one obtains 10.8 g. of N-carbobenzyloxy-4,4-diethoxy-L-proline, ethyl ester as a yellow oil.

(b) N-Carbobenzyloxy-4,4-diethoxy-L-proline

The crude ester from part (a) (10.8 g., 0.03 mole) is saponified with 70 ml. of 1 N sodium hydroxide according to the procedure of Example 4 (b), 30 ml. of ethanol is added in 10 ml. portions to obtain a solution, to give 10.5 g. of a yellow viscous oil. This oil is dissolved in 100 ml. of ether and treated with cyclohexylamine (3.0 g.). On seeding and rubbing, 8.3 g. of the crystalline N-carbobenzyloxy-4,4-diethoxy-L-proline cyclohexylamine salt separates; m.p. 123°–126° (s. 114°) $[\alpha]_D^{26}$ −32° (c, 1% in ethanol). This material is recrystallized from 20 ml. of acetonitrile to give 7.0 g. of the salt as a colorless solid; m.p. 125°–128° (s. 115°) $[\alpha]_D^{26}$ −31° (c, 1% in ethanol).

The N-carbobenzyloxy-4,4-diethoxy-L-proline cyclohexylamine salt is suspended in 40 ml. of ethyl acetate, stirred and treated with 20 ml. of 1 N hydrochloric acid. The layers are separated and the aqueous phase is extracted with additional ethyl acetate (3×40 ml.), the organic layers are combined, dried (MgSO₄), and the solvent evaporated to give 5.6 g. (56%) of N-carbenzyloxy-4,4-diethoxy-L-proline as a light yellow oil.

(c) 4,4-Diethoxy-L-proline

A solution of the N-carbobenzyloxy-4,4-diethoxy-L-proline (5.6 g., 0.017 mole) in 180 ml. of 2:1 ethanol-water is treated with 2 g. of a 5% palladium carbon catalyst and shaken under 3 atmospheres of hydrogen for six hours. The crude partly solid product is rubbed first under ethanol, then ether, and the evaporation repeated each time to give 3 g. (91%) of nearly colorless solid 4,4-diethoxy-L-proline; m.p. 172°–174° (dec.); preceded by gradual darkening and sintering $[\alpha]_D^{26}$ −40° (c, 1% in methanol).

Anal. Calc'd. for C₉H₁₇NO₄.0.25 H₂O: C, 52.03; H, 8.49; N, 6.74. Found: C, 52.22; H, 8.59; N, 6.69.

(d) (S)-1-[3-(acetylthio)-2-methyl-1-oxopropyl]-4,4-diethoxy-L-proline

The 4,4-diethoxy-L-proline (2.9 g., 0.014 mole) from part (c) and 3 g. (0.017 mole) of D-3-acetylthio-2-methylpropionyl chloride dissolved in 3.5 ml. of ether are reacted in 35 ml. of water in the presence of sodium carbonate according to the procedure of Example 3 (d) to yield 5.4 g. of pale yellow viscous oil. This oily product is treated in 40 ml. of ethyl acetate with 2.6 g. of dicyclohexylamine and diluted with 60 ml. of hexane to yield in two crops 4.9 g. of (S)-1-[(3-acetylthio)-2-methyl-1-oxopropyl]-4,4-diethoxy-L-proline dicyclohexylamine salt; m.p. 135°–138° (s. 132°). Following recrystallization from 15 ml. of hot ethyl acetate-45 ml. of hexane, the colorless solid salt weighs 4.2 g.; m.p. 138°–140° (s. 135°), $[\alpha]_D^{26}$ −63° (c, 1% in ethanol).

Anal. Calc'd. for C₁₅H₂₅NO₆S.C₁₂H₂₃N: C, 61.33; H, 9.15; N, 5.30; S, 6.06. Found: C, 61.48; H, 9.55; H, 5.25; S, 5.91.

The dicyclohexylamine salt is converted to the free acid by suspending 4.2 g. in 40 ml. of ethyl acetate, cooling and treating with 40 ml. of 10% potassium bisulfate solution to give two layers. After separating, the aqueous phase is extracted with ethyl acetate (3×50 ml.), the combined organic layers are dried (MgSO₄), and the solvent evaporated to give 3.0 g. (61%) of (S)-1-[3-(acetylthio)-2-methyl-1-oxopropyl]-4,4-diethoxy-L-proline as a pale yellow viscous syrup.

EXAMPLE 6

(S)-4,4-Diethoxy-1-(3-Mercapto-2-methyl-1-oxopropyl)-L-proline

Argon is passed through a cold solution of 5.5 ml of concentrated ammonium hydroxide in 13 ml. of water for 0.25 hour. The latter is then added while cooling under a blanket of argon to 3.0 g. (0.0086 mole) of (S)-1-[3-(acetylthio)-2-methyl-1-oxopropyl]-4,4-diethoxy-L-proline and the mixture is worked up as described in Example 4 to yield 2.4 g. (92%) of (S)-4,4-diethoxy-1-(3-mercapto-2-methyl-1-oxopropyl)-L-proline as a nearly colorless viscous syrup $[\alpha]_D^{26}$ −64°, (c, 1% in ethanol).

Anal. Calc'd. for C₁₃H₂₃NO₅.0.25 H₂O: C, 50.38; H, 7.64; N, 4.52; S, 10.35. Found: C, 50,68; H, 7.96; N, 4.78; S, 10.07.

EXAMPLE 7

[2(S),3S]-2-[3-(Acetylthio)-2-methyl-1-oxopropyl]-6,10-dioxo-2-azaspiro[4.5]decane-3-carboxylic acid (a) N-Carbobenzyloxy-4,4-trimethylenedioxy-L-proline Interaction of 8.2 g. (0.031 mole) of N-carbobenzyloxy-4-keto-L-proline and 45 ml. (0.62 mole) of 1,3-propanediol in 450 ml. of benzene in the presence of 500 mg. of p-toluenesulfonic acid gives 12.3 g. of crude viscous ester product. This product is saponified with 70 ml. of 1 N sodium hydroxide to give 10.6 g. of crude N-carbobenzyloxy-4,4-trimethylenedioxy-L-proline as a yellow oil. The latter is dissolved in 40 ml. of ethanol-400 ml. ether and treated with 3.2 g. of cyclohexylamine to yield 10.1 g. of N-carbobenzyloxy-4,4-trimethylenedioxy-L-proline, cyclohexylamine salt; m.p. 163°–165° (s. 160°), $[\alpha]_D^{26}$ −27° (c, 1% in ethanol). Crystallization of 9.8 g. of the salt from 300 ml. of acetonitrile yields 9.5 g. of colorless solid cyclohexylamine salt; m.p. 165°–167° (s, 162°) $[\alpha]_D^{25}$ −27° (c, 1% in ethanol).

The cyclohexylamine salt (9.0 g.) is suspended in 40 ml. of ethyl acetate, stirred, cooled, and treated with 45 ml. of 1 N hydrochloric acid. The layers are separated, the aqueous phase extracted with additional ethyl acetate (3×40 ml.), the combined organic layers are dried (MgSO₄), and the solvent evaporated to give 7.1 g. (75%) of glass-like N-carbobenzyloxy-4,4-trimethylenedioxy-L-proline.

(b) 4,4-Trimethylenedioxy-L-proline

A solution of 7.1 g. (0.022 mole) of N-carbobenzyloxy-4,4-trimethylenedioxy-L-proline in 200 ml. of 2:1 methanol-water is hydrogenated in the presence of 2 g. of 5% palladium-carbon catalyst to give 3.8 g. (93%) of nearly colorless 4,4-trimethylenedioxy-L-proline;

m.p. 234°–236° (dec.); preceded by gradual darkening and sintering; $[\alpha]_D^{25}$ −36° (c, 0.5% in 1:1 methanol-water).

Anal. Calc'd. for $C_8H_{13}NO_4$: C, 51,33; H, 7.00; N, 7.48. Found: C, 51.42; H, 7.11; N, 7.40.

(c) [2(S),3S]-2-[3-(Acetylthio)-2-methyl-1-oxopropyl]-6,10-dioxo-2-azaspiro[4,5]decane-3-carboxylic acid 4,4-Trimethylenedioxy-L-proline (3.7 g., 0.02 mole) is acylated with 4.0 g. (0.022 mole) of D-3-acetylthio-2-methylpropionyl chloride in 50 ml. of water in the presence of sodium carbonate according to the procedure of Example 1 (e) to give 7.3 g. of glass-like crude product.

The product is converted to its dicyclohexylamine salt with 3.6 g. of dicyclohexylamine in 70 ml. of ethyl acetate. On seeding and rubbing, the crystalline salt precipitates to yield 7.5 g. of dicyclohexylamine salt; m.p. 168°–170° (s. 166°), $[\alpha]_D^{26}$ −59° (c, 1% in ethanol). Recrystallization from 30 ml. of acetonitrile gives 6.5 g. of colorless solid salt; m.p. 169°–171°, $[\alpha]_D^{25}$ −63°, (c, 1% in ethanol).

The dicyclohexylamine salt is converted to the free acid by suspending 6.4 g. in 75 ml. of ethyl acetate and treating with 75 ml. of 10% potassium bisulfate and stirring until two layers are obtained. After separating, the aqueous phase is extracted with ethyl acetate (4×75 ml.), the organic layers are combined, dried (MgSO4), and the solvent evaporated to give 4.3 g. (67%) of glass-like [2(S),3S]-2-[3-(acetylthio)-2-methyl-1-oxopropyl]-6,10-dioxo-2-azaspiro[4,5]decane-3-carboxylic acid.

EXAMPLE 8

[2(S),3S]-2-(3-Mercapto-2-methyl-1-oxopropyl)-6,10-dioxo-2-azaspiro[4,5]decane-3-carboxylic acid

[2(S),3S]-2-[3-(Acetylthio)-2-methyl-1-oxopropyl]-6,10-dioxo-2-azaspiro[4,5]decane-3-carboxylic acid (4.3 g., 0.013 mole) is hydrolyzed with 8.5 ml. of concentrated ammonia in 20 ml. according to the procedure of Example 2 to yield 0.9 g. of colorless solid product; $[\alpha]_D^{25}$ −64° (c, 0.5% in ethanol). An additional 0.8 g. of product is obtained by extracting the aqueous phase with chloroform; $[\alpha]_D^{25}$ −66°. The two crops are dissolved in chloroform, evaporated, rubbed under ether, and the evaporating repeated to yield 1.7 g. (46%) of [2(S),3S]-2-(3-mercepto-2-methyl-1-oxopropyl)-6,10-dioxo-2-azaspiro[4,5]decane-3-carboxylic acid; m.p. 169°–171° (s. 167°), $[\alpha]_D^{26}$ −71° (c, 1% in methanol).

Anal. Calc'd. for $C_{12}H_{19}NO_5S$: C, 49.81; H, 6.62; N, 4.84; S, 11.08. Found: C, 49.67; H, 6.67; N, 4.93; S, 11.10.

EXAMPLE 9

[7(S),8S]-7-[3-(Acetylthio)-2-methyl-1-oxopropyl]-7-aza-1,4-dithiaspiro[4.4]nonane-8-carboxylic acid (a) N-Carbobenzyloxy-4,4-ethylenedithio-L-proline, methyl ester A stirred solution of 3.9 g. (0.014 mole) of N-carbobenzyloxy-4-keto-L-proline, methyl ester in 60 ml. of methylene chloride is treated with 3 ml. (0.036 mole) of ethanedithiol, cooled to 8°, and treated under an argon blanket with 3 ml. (0.024 mole) of boron trifluoride etherate. After removing the cooling bath, the pale yellow solution is stirred for an additional hour and kept overnight at room temperature. The solution is stirred, treated with several pieces of crushed ice, followed by 20 ml. of water. After 30 minutes the layers are separated and the aqueous phase (50 ml.) is extracted with additional methylene chloride (3×30 ml.). The combined organic layers are washed with 50 ml. of saturated sodium chloride solution, dried (MgSO4), and the solvent removed on a rotary evaporator to give 6 g. (100%) of a pale yellow oil N-carbobenzyloxy-4,4-ethylenedithio-L-proline, methyl ester.

(b) N-Carbobenzyloxy-4,4-ethylenedithio-L-proline

The methyl ester product from part (a) (7.4 g., approximately 0.018 mole) is dissolved in 65 ml. of methanol, treated dropwise at −1° to 4° with 14.5 ml. (0.029 mole) of 2 N sodium hydroxide, kept at 0° for one hour, and at room temperature overnight. After removing about half the solvent on a rotary evaporator, the solution is diluted with 125 ml. of water, washed with ether (wash discarded), acidified while cooling with 5 ml. of 1:1 hydrochloric acid to a pH of 2, and extracted with ethyl acetate (4×50 ml.). The combined extracts are washed with 50 ml. of saturated sodium chloride, dried (MgSO4), and the solvent evaporated to give 6 g. of a pale yellow viscous oil. This oil is dissolved in 25 ml. of ethanol, treated with 1.8 g. of cyclohexylamine in 5 ml. of ethanol, and diluted to 300 ml. with ether. On seeding and rubbing, the crystalline cyclohexylamine salt separates to yield after overnight cooling 5.7 g. of N-carbobenzyloxy-4,4-ethylenedithio-L-proline cyclohexylamine salt; m.p. 205°–207° (s. 201°). Recrystallization from 50 ml. of ethanol-400 ml. ether yields 4.9 g. of colorless solid salt; m.p. 207°–209° (s. 201°), $[\alpha]_D^{25}$ −15° (c, 1% in chloroform).

The cyclohexylamine salt (4.8 g.) is suspended in 25 ml. of ethyl acetate, stirred, and treated with 25 ml. of 1 N hydrochloric acid. When two clear layers are obtained, they are separated, the aqueous phase is extracted with additional ethyl acetate (3×25 ml.), the combined organic layers are dried (MgSO4), and the solvent evaporated to give 3.8 g. (62%) of N-carbobenzyloxy-4,4-ethylenedithio-L-proline as a pale yellow viscous syrup.

(c) 4,4-Ethylenedithio-L-proline, hydrobromide

N-Carbobenzyloxy-4,4-ethylenedithio-L-proline (3.7 g., 0.011 mole) is treated with 20 ml. of hydrogen bromide in acetic acid (30–32%), stoppered loosely, and stirred magnetically. Mixing is difficult due to the viscosity of the starting material and the latter is broken up as much as possible with a spatula. In the meantime, the crystalline product begins to separate. Further quantities of hydrogen bromide in acetic acid are added after 15 minutes (10 ml.) and after 25 minutes (5 ml.) and stirring is continued for a total of 35 minutes. Ether (250 ml.) is added to complete precipitation of the product and after cooling for 15 minutes the cream colored material is filtered under nitrogen, washed with ether, and dried in vacuo to give 2.7 g. of 4,4-ethylenedithio-L-proline, hydrobromide; m.p. 240°–242° (dec.); sintering and darkening from approximately 200°; $[\alpha]_D^{26}$ −40° (c, 0.5% in 1:1 chloroform-methanol).

(d) [7(S),8S]-7-[3-(Acetylthio)-2-methyl-1-oxopropyl]-7-aza-1,4-dithiaspiro[4.4]nonane-8-carboxylic acid A stirred solution of 2.6 g. (0.0091 mole) of 4,4-ethylenedithio-L-proline, hydrobromide in 25 ml. of water is cooled to 5° and brought to pH 8.2 by the addition of 25% sodium carbonate (wt./vol.). While continuing stirring and cooling, a solution of 1.9 g. (0.01 mole) of D-3-acetylthio-2-methylpropionyl chloride in 2.5 ml. of ether is added portionwise while maintaining the pH at 7.5–8.2 by the dropwise addition of 25% sodium carbonate. When the pH is stabilized at 8.2–8.5

(after about 15 minutes), stirring and cooling are continued for a total of one hour. The solution is then washed with 25 ml. of ethyl acetate (wash discarded), layered over with 25 ml. of ethyl acetate, cooled, stirred, acidified carefully with 1:1 hydrochloric acid to pH 2.0, saturated with sodium chloride, and the layers separated. The aqueous phase is extracted with additional ethyl acetate (3×25 ml.), the combined organic layers dried (MgSO$_4$), and the solvent evaporated, finally at 0.2 mm., to give 2.6 g. of syrupy product which begins to crystallize. The latter is treated in 30 ml. of ethyl acetate with 1.5 g. of dicyclohexylamine to give 3.0 g. of colorless dicyclohexylamine salt; m.p. 176°–178° (s, 170°); $[\alpha]_D^{26}$ −55° (c, 1% in ethanol). This material is ground in a mortar under 15 ml. of acetonitrile, cooled for one hour, filtered, washed with 5 ml. of cold acetonitrile and with ether, and dried to give 2.9 g. of dicyclohexylamine salt; m.p. 177°–179° (s, 172°); $[\alpha]_D^{26}$ −56° (c, 1% in ethanol).

Anal. Calc'd. for $C_{13}H_{19}NO_4S \cdot C_{12}H_{23}N$: C, 56.56; H, 7.98; N, 5.28; S, 18.12. Found: C, 56.21; H, 8.18; N, 5.05; S, 18.00.

The above dicyclohexylamine salt is converted to the free acid by suspending 2.8 g. in 30 ml. of ethyl acetate, cooling, and treating with 30 ml. of 10% potassium bisulfate to give two clear layers. After separating, the aqueous phase is extracted with ethyl acetate (3×30 ml.), the combined organic layers dried (MgSO$_4$), and the solvent evaporated, finally at 0.1–0.2 mm and 45°, to give 2.0 g. (63%) of colorless solid [7(S),8S]-7-[3-(acetylthio)-2-methyl-1-oxopropyl]-7-aza-1,4-dithiaspiro[4.4]nonane-8-carboxylic acid, m.p., 125°–126° (s, 122°); $[\alpha]_D^{26}$ −101°(c, 1% in ethanol).

EXAMPLE 10

[7(S),8S]-7-(3-Mercapto-2-methyl-1-oxopropyl)-7-aza-1,4-dithiaspiro[4.4]nonane-8-carboxylic acid Argon is passed through a cold solution of 3.5 ml. of concentrated ammonia in 8.5 ml. of water for 15 minutes. The latter is then added while cooling and under a blanket of argon to 1.9 g. (0.0054 mole) of [7(S),8S]-7-[3-(acetylthio)-2-methyl-1-oxopropyl]-7-aza-1,4-dithiaspiro[4.4]nonane-8-carboxylic acid and the mixture is swirled in an ice-bath until a solution is obtained. Stirring under argon is continued at room temperature for an additional two hours, then the solution is extracted with 15 ml. of ethyl acetate under an argon atmosphere. The aqueous layer is cooled, stirred, layered over with 15 ml. of ethyl acetate, and acidified portionwise with approximately 6.5 ml. of 1:1 hydrochloric acid. The layers are separated, the aqueous phase extracted with additional ethyl acetate (3×15 ml.), the combined acetate layers dried (MgSO$_4$), and the solvent evaporated to give a glass-like residue which solidifies when rubbed under ether. The evaporation is repeated and the colorless product is suspended in 30 ml. of hexane, filtered and dried in vacuo to give 1.4 g. (84%) of [7(S),8S]-7-(3-mercapto-2-methyl-1-oxopropyl)-7-aza-1,4-dithiaspiro[4.4]nonane-8-carboxylic acid; m.p. 116°–118° (s, 105°); $[\alpha]_D^{26}$ −44° (c, 1% in ethanol).

Anal. Calc'd. for $C_{11}H_{17}NO_3S_3$: C, 42.97; H, 5.57; N, 4.56; S, 31.29; SH, 100%. Found: C, 42.70; H, 5.71; N, 4.54; S, 31.16; SH, 100%.

EXAMPLE 11

[7(S),8S]-7-(3-Mercapto-2-methyl-1-oxopropyl)-1,4-dioxo-7-azaspiro[4.5]decane-8-carboxylic acid (a) [7(S),8S]-7-[3-(Acetylthio)-2-methyl-1-oxopropyl]-1,4-dioxo-7-azaspiro[4.5]decane-8-carboxylic acid Following the procedure of Example 1 but substituting and equivalent amount of N-carbobenzyloxy-5-keto-L-pipecolic acid for the N-carbobenzyloxy-4-keto-L-proline in part (c) and then following the procedure of parts (d) and (e) one obtains, [7(S),8S]-7-[3-(acetylthio)-2-methyl-1-oxopropyl]-1,4-dioxo-7-azaspiro[4.5]decane-8-carboxylic acid.

(b) [7(S),8S]-7-(3-Mecapto-2-methyl-1-oxopropyl)-1,4-dioxo-7-azaspiro[4.5]decane-8-carboxylic acid The product from part (a) is hydrolyzed with concentrated ammonia according to the procedure of Example 2 to yield [7(S),8S]-7-(3-mercepto-2-methyl-1-oxopropyl)-1,4-dioxo-7-azaspiro[4.5]decane-8-carboxylic acid.

EXAMPLE 12

[1(S),2S]-1-(3-Mercapto-2-methyl-1-oxopropyl)-5,5-dimethoxy-2-piperidinecarboxylic acid (a) [1(S),2S]-1-[3-(Acetylthio-2-methyl-1-oxopropyl]-5,5-dimethoxy-2-piperidinecarboxylic acid Following the procedure of Example 3 but substituting an equivalent amount of N-carbobenzyloxy-5-keto-L-pipecolic acid for the N-carbobenzyloxy-4-keto-L-proline in part (a) one obtains [1(S),2S]-1-[3-(acetylthio)-2-methyl-1-oxopropyl]-5,5-dimethoxy-2-piperidinecarboxylic acid.

(b) [1(S),2S]-1-(3-Mercapto-2-methyl-1-oxopropyl)-5,5-dimethoxy-2-piperidinecarboxylic acid The product from part (a) is hydrolyzed with concentrated ammonia according to the procedure of Example 4 to yield [1(S),2S]-1-(3-mercapto-2-methyl-1-oxopropyl)-5,5-dimethoxy-2-piperidinecarboxylic acid.

EXAMPLE 13

[1(S),2±]-1-(3-Mercapto-2-methyl-1-oxopropyl)-4,4-dimethoxy-2-piperidinecarboxylic acid (a) [1(S),2±]-1-[3-(Acetylthio)-2-methyl-1-oxopropyl]-4,4-dimethoxy-2-piperidinecarboxylic acid Following the procedure of Example 3 but substituting an equivalent amount of N-carbobenzyloxy-4-keto-2-pipecolic acid bor the N-carbobenzyloxy-4-keto-L-proline in part (a) one obtains [1(S),2±]-1-[3-(acetylthio)-2-methyl-1-oxopropyl]-4,4-diethoxy-2-piperidinecarboxylic acid.

(b) [1(S),2±]-1-(3-Mercapto-2-methyl-1-oxopropyl)-4,4-dimethoxy-2-piperidinecarboxylic acid The product from part (a) is hydrolyzed with concentrated ammonia according to the procedure of Example 4 to yield [1(S),2±]-1-(3-mercapto-2-methyl-1-oxopropyl)-4,4-dimethoxy-2-piperidinecarboxylic acid.

EXAMPLE 14

[2(S),3S]-2-(3-Mercapto-2-methyl-1-oxopropyl)-6,10-dithia-2-azaspiro[4.5]decane-3-carboxylic acid (a) [2(S),3S]-2-(3-(Acetylthio)-2-methyl-1-oxopropyl)-6,10-dithia-2-azaspiro[4.5]decane-3-carboxylic acid Following the procedure of Example 9 but substituting 1,3-propanedithiol for the ethanedithiol in part (a), one obtains [2(S),3S]-2-[3-(acetylthio)-2-methyl-1-oxopropyl]-6,10-dithio-2-azaspiro[4.5]decane-3-carboxylic acid.

(b) [2(S),3S]-2-(3-Mercapto-2-methyl-1-oxopropyl)-6,10-dithia-2-azaspiro[4.5]decane-3-carboxylic acid The product from part (a) is hydrolyzed with concentrated ammonia according to the procedure of Example 10 to yield [2(S),3S]-2-(3-mercapto-2-methyl-1-oxopropyl)-6,10-dithia-2-azaspiro[4.5]decane-3-carboxylic acid.

EXAMPLE 15

[7(S),8S]-7-(3-Mercapto-2-methyl-1-oxopropyl)-1-oxo-4-thia-7-azaspiro[4.4]nonane-8-carboxylic acid (a) [7(S),8S]-7-[3-(Acetylthio)-2-methyl-1-oxopropyl]-1-oxo-4-thia-7-azaspiro[4.4]nonane-8-carboxylic acid Following the procedure of Example 1 but substituting 2-mercaptoethanol for the ethylene glycol in part (c), one obtains [7(S).8S]-7-[3-(acetylthio)-2-methyl-1-oxopropyl]-1-oxo-4-thia-7-azaspiro[4.4]nonane-8-carboxylic acid.

(b) [7(S),8S]-7-(3-Mercapto-2-methyl-1-oxopropyl)-1-oxo-4-thia-7-azaspiro[4.4]nonane-8-carboxylic acid The product from part (a) is hydrolyzed with concentrated ammonia according to the procedure of Example 2 to yield [7(S),8S]-7-(3-mercapto-2-methyl-1-oxopropyl)-1-oxo-4-thia-7-azaspiro[4.4]nonane-8-carboxylic acid.

EXAMPLE 16

(8S)-7-[3-(Acetylthio)-2-trifluoromethyl-1-oxopropyl]-1,4-dioxo-7-azaspiro[4.4]nonane-8-carboxylic acid (Isomers A and B)

(a) D,L-3-(Acetylthio)-2-trifluoromethylpropionic acid

α-Trifluoromethyl acrylic acid (10 g., 0.071 mole) [prepared according to the procedure set forth J. Chem. Soc., 1954, p. 371] is cooled in a salt-ice-water bath, stirred and treated portionwise with 5.7 ml. (0.075 mole) of 97% thiolacetic acid. After the addition, the yellow liquid is stirred in the cold for one hour, allowed to warm to room temperature, and distilled to yield 14 g. (91%) of D,L-3-(acetylthio)-2-trifluoromethylpropionic acid as a light yellow oil, b.p. 149°–153°/13 mm. The material solidifies on storing in the cold.

(b) D,L-3-(Acetylthio)-2-trifluoromethylpropionyl chloride

The D,L-3-(acetylthio)-2-trifluoromethylpropionyl acid (7 g., 0.032 mole) is treated with 18 ml. (0.25) of redistilled thionyl chloride and the mixture is refluxed for three hours. After removing the excess thionyl chloride on a rotary evaporator, the residue is distilled to give 6.8 g. of D,L-3-(acetylthio)-2-trifluoromethylpropionyl chloride as a pale yellow oil; b.p. 80°–82°/16 mm.

(c) (8S)-7-(Acetylthio)-2-trifluoromethyl-1-oxopropyl]-1,4-dioxo-7-azaspiro[4.4]nonane-8-carboxylic acid (Isomers A and B)

4,4-Ethylenedioxy-L-proline (2.4 g., 0.014 mole) is reacted with 3.4 g. (0.014 mole) of D,L-3-(acetylthio)-2-trifluoromethylpropionyl chloride in 40 ml. of water in the presence of sodium carbonate according to the procedure of Example 1 (e) to yield 4.5 g. of nearly colorless solid product; m.p. 126°–145° (s. 115°), $[\alpha]_D^{25} -34°$ (c, 1% in ethanol).

The mixture of diastereoisomers (4.2 g.) is suspended in 45 ml. of ether, stirred for two hours, cooled for 20 minutes, and the undissolved solid is filtered, washed with cold ether, and air dried to yield 2.7 g. of product; m.p. 166°–172° (s. 140°), $[\alpha]_D^{25} -62°$ (c, 1% in ethanol). The material is then ground in a mortar under 25 ml. of ether, filtered after 15 minutes, washed with some ether, and again air-dried to yield 2.1 g. of product; m.p. 172°–177° (s. 143°). Following crystallization from 11 ml. of boiling isopropanol and cooling overnight, 1.55 g. of colorless (8S)-7-[3-(acetylthio)-2-trifluoromethyl-1-oxopropyl]-1,4-dioxo-7-azaspiro[4.4]-nonane-8-carboxylic acid, isomer A is obtained; m.p. 192°–194° (s, 183°), $[\alpha]_D^{25} -32°$ (c, 1% in ethanol). A sample is recrystallized from isopropanol; m.p. 193°–195° (s, 184°), $[\alpha]_D^{25} -134°$ (c, 1% in ethanol).

Isomer B is obtained by combining the above ether and isopropanol filtrates and removing the solvents under reduced pressure to give 2.2 g. of a pale yellow solid; m.p. 108°–109° (s, 95°); $[\alpha]_D^{25} +30°$ (c, 1% in ethanol). This material is purified by crystallization from 6 ml. of isopropanol to give 1.2 g. of nearly colorless solid; m.p. 153°–155° (s, 130°), $[\alpha]_D^{25} +40°$ (c, 1% in ethanol). After crystallization from 4 ml. of ethyl acetate −6 ml. of hexane, 1.1 g. of (8S)-7-[3-(acetylthio)-2-trifluoromethyl-1-oxopropyl]-1,4-dioxo-7-azaspiro[4.4-]nonane-8-carboxylic acid, isomer B; m.p. 153°–155° (s, 141°), $[\alpha]_D^{25} +41°$ (c, 1% in ethanol) is obtained.

EXAMPLE 17

(8S)-7-(3-Mercapto-2-trifluoromethyl-1-oxopropyl)-1,4-dioxo-7-azaspiro[4.4]nonane-8-carboxylic acid, Isomer A Isomer A product from Example 16 (1.45 g., 0.0039 mole) is hydrolyzed with 2.5 ml. of concentrated ammonia in 6 ml. of water over a period of one hour as described in Example 2 to yield 1.25 g. (97%) of colorless (8S)-7-(3-mercapto-2-trifluoromethyl-1-oxopropyl)-1,4-dioxo-7-azaspiro[4.4]nonane-8-carboxylic acid, isomer A, as a glass-like product, $[\alpha]_D^{25} -61°$ (c, 1% in ethanol). TLC: $R_f$ 0.40 (95:5:5 methylene chloride-methanol-acetic acid; vis. SH reagent, PMA and heat).

Anal. Calc'd for $C_{11}H_{14}F_3NO_5S$: C, 40.12; H, 4.28; N, 4.25; S, 9.74; F, 17.31. Found: C, 40.10, H, 4.43; N, 4.51; S, 9.63; F, 17.10.

The above acid is dissolved in ethyl acetate and treated with 1-adamantanamine to yield the 1-adamantanamine salt; m.p. 213°–215° (dec.), $[\alpha]_D^{25} -47°$ (c, 1% in methanol).

EXAMPLE 18

(8S)-7-(2-Mercapto-2-trifluoromethyl-1-oxopropyl)-1,4-dioxo-7-azaspiro[4.4]nonane-8-carboxylic acid, Isomer B Isomer B product from Example 16 (1.05 g., 0.0028 mole) is hydrolyzed with 2 ml. of concentrated ammonia in 5 ml. of water according to the procedure described in Example 2 to yield 0.9 g. (97%) of (8S)-7-(3-mercapto-2-trifluoromethyl-1-oxopropyl)-1,4-dioxo-7-azaspiro[4.4]nonane-8-carboxylic acid, Isomer B as a pale yellow viscous syrup; $[\alpha]_D^{25} -16°$ (c, 1% in ethanol). The material sets to a waxy solid; m.p. 61°–64° (s 55°)

Anal. Calc'd. for: $C_{11}H_{14}F_3NO_5S.0.25 H_2O$: C, 39.58; H, 4.38; N, 4.20; S, 9.61; F, 17.01. Found: C, 39.60; H, 4.28; N, 4.26; S, 9.62; F, 16.89.

EXAMPLE 19

1-[3-(Acetylthio)-2-trifluoromethyl-1-oxopropyl]-4,4-dimethoxy-L-proline, Isomers A and B Following the procedure of Example 16 but substituting 4,4-dimethoxy-L-proline for the 4,4-ethylenedioxy-L-proline in part (c), one obtains 1-[3-(acetylthio)-2-trifluoromethyl-1-oxopropyl]-4,4-dimethoxy-L-proline as a racemic mixture. The individual isomers can be separated as taught in Example 16.

EXAMPLE 20

1-(3-Mercapto-2-trifluoromethyl-1-oxopropyl)-4,4-dimethoxy-L-proline, Isomer A and Isomer B Each individual isomer product from Example 19 is hydrolyzed with concentrated ammonia according to the procedure of Example 4 to yield 1-(3-mercapto-2-trifluoromethyl-1-oxopropyl)-4,4-dimethoxy-L-proline, isomer A and 1-(3-mercapto-2-trifluoromethyl-1-oxopropyl)-4,4-dimethoxy-L-proline, isomer B.

EXAMPLE 21

[7(S),8S]-7-(3-Mercapto-2-mercaptomethyl-1-oxopropyl)-1,4-dioxo-7-azaspiro[4.4]nonane-8-carboxylic acid (a) [7(S),8S]-7-[3-(Acetylthio)-2-(acetylthiomethyl)-1-oxopropyl]-1,4-dioxo-7-azaspiro[4.4]nonane-8-carboxylic acid Following the procedure of Example 1 but substituting D-2-acetylthiomethyl-3-acetylthiopropionyl chloride for the D-3-acetylthio-2-methylpropionyl chloride in part (e), one obtains [7(S),8S]-7-[3-(acetylthio)-2-(acetylthiomethyl)-1-oxopropyl]-1,4-dioxo-7-azaspiro[4.4]nonane-8-carboxylic acid.

(b) [7(S),8(S)]-7-(3-Mercapto-2-mercaptomethyl-1-oxopropyl)-1,4-dioxo-7-azaspiro[4.4]nonane-8-carboxylic acid The product from part (a) is hydrolyzed with concentrated ammonia according to the procedure of Example 2 to yield [7(S),8S]-7-(3-mercapto-2-mercaptomethyl-1-oxopropyl)-1,4-dioxo-7-azaspiro[4.4]nonane-8-carboxylic acid.

EXAMPLE 22

(S)-1-(3-Mercapto-2-mercaptomethyl-1-oxopropyl)-4,4-dimethoxy-L-proline (a) (S)-1-[3-(Acetylthio)-2-(acetylthiomethyl)-1-oxopropyl]-4,4-dimethoxy-L-proline Following the procedure of Example 3 but substituting D-2-acetylthiomethyl-3-acetylthiopropionyl chloride for the D-3-acetylthio-2-methylpropionyl chloride in part (d), one obtains (S)-1-[3-(acetylthio)-2-(acetylthiomethyl)-1-oxopropyl]-4,4-dimethoxy-L-proline.

(b) (S)-1-(3-Mercapto-2-mercaptomethyl-1-oxopropyl)-4,4-dimethoxy-L-proline

The product from part (a) is hydrolyzed with concentrated ammonia according to the procedure of Example 4 to yield (S)-1-(3-mercapto-2-mercaptomethyl-1-oxopropyl)-4,4-dimethoxy-L-proline.

EXAMPLE 23

(8S)-7-(3-Mercapto-2-methylthio-1-oxopropyl)-1,4-dioxo-7-azaspiro[4.4]nonane-8-carboxylic acid (a) 3-(Acetylthio)-2-(methylthio)propionic acid 12.5 g. (0.094 mole) of methyl-2-(methylthio)acrylate [prepared from methyl 2-chloroacrylate according to the procedure of Gundesmann et al., Chemische Berichte 94, 3254 (1916)] is stirred with 1 N aqueous sodium hydroxide (94 ml.) with ice cooling. The mixture is allowed to warm to ambient temperature, then stirred for five hours. The resulting solution is washed with ether, then acidified to pH 2 with concentrated hydrochloric acid. The solid precipitate is extracted into methylene chloride, and the solution is washed with saturated sodium chloride and the solvent evaporated. The solid residue, 2-(methylthio)acrylic acid; m.p. 70°–75°, is used immediately in the following reaction.

Equimolar amounts of 2-(methylthio)acrylic acid and thiolacetic acid are mixed under argon and stirred at 80° for several hours to yield 3-(acetylthio)-2-(methylthio)propionic acid.

(b) 3-(Acetylthio)-2-(methylthio)propionic acid chloride

The 3-(acetylthio)-2-(methylthio)propionic acid is refluxed in thionyl chloride for two hours. The reaction mixture is distilled to remove excess thionyl chloride and the product is distilled in vacuo to yield 3-(acetylthio)-2-(methylthio)propionic acid chloride.

(c) (8S)-7-[3-(Acetylthio)-2-methylthio-1-oxopropyl]-1,4-dioxo-7-azaspiro[4.4]nonane-8-carboxylic acid 4,4-Ethylenedioxy-L-proline is reacted with 3-(acetylthio)-2-(methylthio)propionic acid chloride according to the procedure of Example 1 (e) to yield (8S)-7-[3-(acetylthio)-2-methylthio-1-oxopropyl]-1,4-dioxo-7-azaspiro[4.4]nonane-8-carboxylic acid.

(d) (8S)-7-(3-Mercapto-2-methylthio-1-oxopropyl)-1,4-dioxo-7-azaspiro[4.4]nonane-8-carboxylic acid The product from part (c) is treated with concentrated ammonia according to the procedure of Example 2 to yield (8S)-7-(3-mercapto-2-methylthio-1-oxopropyl)-1,4-dioxo-7-azaspiro[4.4]nonane-8-carboxylic acid.

EXAMPLE 24

1-(3-Mercapto-2-methylthio-1-oxopropyl)-4,4-dimethoxy-L-proline (a) 1-[3-(Acetylthio)-2-methylthio-1-oxopropyl]-4,4-dimethoxy-L-proline 4,4-Dimethoxy-L-proline is reacted with 3-(acetylthio)-2-(methylthio)propionic acid chloride according to the procedure of Example 3 (d) to yield 1-[3-(acetylthio)-2-methylthio-1-oxopropyl]-4,4-dimethoxy-L-proline.

(b) 1-(3-Mercapto-2-methylthio-1-oxopropyl)-4,4-dimethoxy-L-proline

The product from part (a) is hydrolyzed with concentrated ammonia according to the procedure of Example 4 to yield 1-(3-mercapto-2-methylthio-1-oxopropyl)-4,4-dimethoxy-L-proline.

EXAMPLE 25

(8S)-7-(3-Mercapto-1-oxopropyl)-1,4-dioxo-7-azaspiro[4.4]nonane-8-carboxylic acid (a) (8S)-7-[3-(Acetylthio)-1-oxopropyl]-1,4-dioxo-7-azaspiro[4.4]nonane-8-carboxylic acid 4,4-Ethylenedioxy-L-proline is reacted with 3-acetylthiopropionyl chloride according to the procedure of Example 1 (e) to yield (8S)-7-[3-(acetylthio)-1-oxopropyl]-1,4-dioxo-7-azaspiro[4.4]nonane-8-carboxylic acid.

(b) (8S)-7-(3-Mercapto-1-oxopropyl)-1,4-dioxo-7-azaspiro[4.4]nonane-8-carboxylic acid The product from part (a) is hydrolyzed with concentrated ammonia according to the procedure of Example 2 to yield (8S)-7-(3-mercapto-1-oxopropyl)-1,4-dioxo-7-azaspiro[4.4]nonane-8-carboxylic acid.

EXAMPLE 26

1-(3-Mercapto-1-oxopropyl)-4,4-dimethoxy-L-proline (a) 1-[3-(Acetylthio)-1-oxopropyl]-4,4-dimethoxy-L-proline 4,4-Dimethoxy-L-proline is reacted with 3-acetylthiopropionyl chloride according to the procedure of Example 3 (d) to yield 1-[3-(acetylthio)-1-oxopropyl]-4,4-dimethoxy-L-proline.

(b) 1-(3-Mercapto-1-oxopropyl)-4,4-dimethoxy-L-proline

The product from part (a) is hydrolyzed with concentrated ammonia according to the procedure of Example 4 to yield 1-(3-mercapto-1-oxopropyl)-4,4-dimethoxy-L-proline.

EXAMPLE 27

(8S)-7-(4-Mercapto-1-oxobutyl)-1,4-dioxo-7-azaspiro[4.4]nonane-8-carboxylic acid (a) (8S)-7-[4-(Acetylthio)-1-oxobutyl]-1,4-dioxo-7-azaspiro[4.4]nonane-8-carboxylic acid 4,4-Ethylenedioxy-L-proline is reacted with 4-acetylthiobutyroyl chloride according to the procedure of Example 1 (e) to yield 8(S)-7-[4-(acetylthio)-1-oxobutyl]-1,4-dioxo-7-azaspiro[4.4]nonane-8-carboxylic acid.

(b) (8S)-7-(4-Mercapto-1-oxobutyl)-1,4-dioxo-7-azaspiro[4.4]nonane-8-carboxylic acid The product from part (a) is hydrolyzed with concentrated ammonia according to the procedure of Example 2 to yield (8S)-7-(4-mercapto-1-oxobutyl)-1,4-dioxo-7-azaspiro[4.4]nonane-8-carboxylic acid.

EXAMPLE 28

1-(4-Mercapto-1-oxobutyl)-4,4-dimethoxy-L-proline (a) 1-[4-(Acetylthio)-1-oxobutyl]-4,4-dimethoxy-L-proline 4,4-Dimethoxy-L-proline is reacted with 4-acetylthiobutyroyl chloride according to the procedure of Example 3 (d) to yield 1-[4-(acetylthio)-1-oxobutyl]-4,4-dimethoxy-L-proline.

(b) 1-(4-Mercapto-1-oxobutyl)-4,4-dimethoxy-L-proline

The product from part (a) is hydrolyzed with concentrated ammonia according to the procedure of Example 4 to yield 1-(4-mercapto-1-oxobutyl)-4,4-dimethoxy-L-proline.

EXAMPLE 29

(8S)-7-(2-Mercapto-1-oxoethyl)-1,4-dioxo-7-azaspiro[4.4]nonane-8-carboxylic acid (a) (8S)-7-[2-(Acetylthio)-1-oxoethyl]-1,4-dioxo-7-azaspiro[4.4]nonane-8-carboxylic acid 4,4-Ethylenedioxy-L-proline is reacted with acetylthioacetyl chloride according to the procedure of Example 1 (e) to yield (8S)-7-[2-(acetylthio)-1-oxoethyl]-1,4-dioxo-7-azaspiro[4.4]nonane-8-carboxylic acid.

(b) (8S)-7-(2-Mercapto-1-oxoethyl)-1,4-dioxo-7-azaspiro[4.4]nonane-8-carboxylic acid The product from part (a) is hydrolyzed with concentrated ammonia according to the procedure of Example 2 to yield (8S)-7-(2-mercapto-1-oxoethyl)-1,4-dioxo-7-azaspiro[4.4]nonane-8-carboxylic acid.

EXAMPLE 30

1-(2-Mercapto-1-oxoethyl)-4,4-dimethoxy-L-proline (a) 1-[2-(Acetylthio)-1-oxoethyl]-4,4-dimethoxy-L-proline 4,4-Dimethoxy-L-proline is reacted with acetylthioacetyl chloride according to the procedure of Example 3 (d) to yield 1-[2-(acetylthio)-1-oxoethyl]-4,4-dimethoxy-L-proline.

(b) 1-(2-Mercapto-1-oxoethyl)-4,4-dimethoxy-L-proline

The product from part (a) is hydrolyzed with concentrated ammonia according to the procedure of Example 4 to yield 1-(2-mercapto-1-oxoethyl)-4,4-dimethoxy-L-proline.

EXAMPLE 31

(8S)-7-(3-Mercapto-2,2-dimethyl-1-oxopropyl)-1,4-dioxo-7-azaspiro[4.4]nonane-8-carboxylic acid (a) (8S)-7-[3-(Acetylthio)-2,2-dimethyl-1-oxopropyl]-1,4-dioxo-7-azaspiro[4.4]nonane-8-carboxylic acid 4,4-Ethylenedioxy-L-proline is reacted with 3-acetylthio-2,2-dimethylpropionyl chloride according to the procedure of Example 1 (e) to yield (8S)-7-[3-(acetylthio)-2,2-dimethyl-1-oxopropyl]-1,4-dioxo-7-azaspiro[4.4]nonane-8-carboxylic acid.

(b) (8S)-7-(3-Mercapto-2,2-dimethyl-1-oxopropyl)-1,4-dioxo-7-azaspiro[4.4]nonane-8-carboxylic acid The product from part (a) is hydrolyzed with concentrated ammonia to yield (8S)-7-(3-mercapto-2,2-dimethyl-1-oxopropyl)-1,4-dioxo-7-azaspiro[4.4]nonane-8-carboxylic acid.

EXAMPLE 32

1-(3-Mercapto-2,2-dimethyl-1-oxopropyl)-4,4-dimethoxy-L-proline (a) 1-[3-(Acetylthio)-2,2-dimethyl-1-oxopropyl]-4,4-dimethoxy-L-proline 4,4-Dimethoxy-L-proline is reacted with 3-acetylthio-2,2-dimethylpropionyl chloride according to the procedure of Example 3 (d) to give 1-[3-(acetylthio)-2,2-dimethyl-1-oxopropyl]-4,4-dimethoxy-L-proline.

(b) 1-(3-Mercapto-2,2-dimethyl-1-oxopropyl)-4,4-dimethoxy-L-proline

The product from part (a) is hydrolyzed with concentrated ammonia according to the procedure of Example 4 to give 1-(3-mercapto-2,2-dimethyl-1-oxopropyl)-4,4-dimethoxy-L-proline.

EXAMPLE 33

[7(S),8S]-7-(3-Mercapto-2-ethyl-1-oxopropyl)-1,4-dioxo-7-azaspiro[4.4]nonane-8-carboxylic acid (a) [7(S),8S]-7-[3-(Acetylthio)-2-ethyl-1-oxopropyl]-1,4-dioxo-7-azaspiro[4.4]nonane-8-carboxylic acid 4,4-Ethylenedioxy-L-proline is reacted with D-3-acetylthio-2-ethylpropionyl chloride according to the procedure of Example 1 (e) to give [7(S),8S]7-[3-(acetylthio)-2-ethyl-1-oxopropyl]-1,4-dioxo-7-azaspiro[4.4]nonane-8-carboxylic acid.

(b) [7(S),8S]-7-(3-Mercapto-2-ethyl-1-oxopropyl)-1,4-dioxo-7-azaspiro[4.4]nonane-8-carboxylic acid The product from part (a) is hydrolyzed with concentrated ammonia according to the procedure of Example 2 to give [7(S),8S]-7-(3-mercapto-2-ethyl-1-oxopropyl)-1,4-dioxo-7-azaspiro[4.4]nonane-8-carboxylic acid.

EXAMPLE 34

(S)-1-(3-Mercapto-2-ethyl-1-oxopropyl-4,4-dimethoxy-L-proline (a) (S)-1-[3-(Acetylthio)-2-ethyl-1-oxopropyl]-4,4-dimethoxy-L-proline 4,4-Dimethoxy-L-proline is reacted with D-3-acetylthio-2-ethylpropionyl chloride according to the procedure of Example 3 (d) to give (S)-1-[3-(acetylthio)-2-ethyl-1-oxopropyl]-4,4-dimethoxy-L-proline.

(b) (S)-1-(3-Mercapto-2-ethyl-1-oxopropyl)-4,4-dimethoxy-L-proline

The product from part (a) is hydrolyzed with concentrated ammonia according to the procedure of Example 4 to give (S)-1-(3-mercapto-2-ethyl-1-oxopropyl)-4,4-dimethoxy-L-proline.

EXAMPLE 35

[8S]-7-(3-Mercapto-2-trifluoromethyl-1-oxopropyl)-7-aza-1,4-dithiaspiro[4.4]nonane-8-carboxylic acid (a) 3-[[(4-Methoxy)phenylmethyl]thio]-2-trifluoromethylpropionyl chloride A neat mixture of 1-trifluoromethylacrylic acid (3.9 g.) and 4-methoxybenzylthiol (4.3 g.) is stirred at 100°-110° for one hour. The mixture is allowed to cool to room temperature and the solid is recrystallized from cyclohexane to yield 3-[[(4-methoxy)phenylmethyl]thio]-2-trifluoromethylpropionic acid; m.p. 72°-74°.

Treatment of this acid with thionyl chloride yields 3-[[(4-methoxy)phenylmethyl]thio]-2-trifluoromethylprpionyl chloride.

(b) [8S]-7-[3-[[(4-Methoxy)phenylmethyl]thio]-2-trifluoromethyl-1-oxopropyl]-7-aza-1,4-dithiaspiro-[4.4]nonane-8-carboxylic acid The 3-[[(4-methoxy)phenylmethyl]thio]-2-trifluoromethyl propionyl chloride from part (a) is reacted with 4,4-ethylenedithio-L-proline according to the procedure of Example 9 (d) to yield [8S]7-[3-[[(4-methoxy)phenylmethyl]thio]-2-trifluoromethyl-1-oxopropyl[-7-aza-1,4-dithiaspiro[4.4]nonane-8-carboxylic acid.

(c) [8S]-7-(3-Mercapto-2-trifluoromethyl-1-oxopropyl)-7-aza-1,4-dithiaspiro[4.4]nonane-8-carboxylic acid The product from part (b) is mixed with tri-fluoroacetic acid and anisole under nitrogen. The solvents are removed under vacuum to yield as a residue [B 8S]-7-(3-mercapto-2-trifluoromethyl-1-oxopropyl)-7-aza-1,4-dithiaspiro[4.4]nonane-8-carboxylic acid.

EXAMPLE 36

[8S]-7-(3-Mercapto-2-methylthio-1-oxopropyl)-7-aza-1,4-dithiaspiro[4.4]nonane-8-carboxylic acid (a) 3-[[(4-Methoxy)phenylmethyl]thio]-2-methylthio-propionyl chloride 3-[[(4-Methoxy)phenylmethyl]thio]-2-methylthiopropanoic acid prepared according to the procedure of Example 10 in U.S. Pat. No. 4,116,962 is treated with thionyl chloride to yield 3-[[(4-methoxy)phenylmethyl]thio]-2-methylthiopropionyl chloride.

(b) [8S]-7-[3-[[(4-Methoxy)phenylmethyl]thio]-2-methylthio-1-oxopropyl]-7-aza-1,4-dithiaspiro[4.4]-nonane-8-carboxylic acid The 3-[[(4-methoxy)phenylmethyl]thio]-2-methylthiopropionyl chloride from part (a) is reacted with 4,4-ethylenedithio-L-proline according to the procedure of Example 9 (d) to yield [8S]-7-[3-[[(4-methoxy)phenylmethyl]thio]-2-methylthio-1-oxopropyl]-7-aza-1,4-dithiaspiro[4.4]nonane-8-carboxylic acid.

(c) [8S]-7-(3-Mercapto-2-methylthio-1-oxo-propyl)-7-aza-1,4-dithiaspiro[4.4]nonane-8-carboxylic acid The product from part (b) is mixed with trifluoroacetic acid and anisole under nitrogen. The solvents are removed under vacuum to yield as a residue [8S]-7-(3-mercapto-2-methylthio-1-oxo-propyl)-7-aza-1,4-dithiaspiro[4.4]nonane-8-carboxylic acid.

EXAMPLE 37

[7(S), 8S]-7-(3-Mercapto-3-methyl-1-oxopropyl)-1,4-dioxo-7-azaspiro[4.4]nonane-8-carboxylic acid (a) [7(S),8S]-7-[3-(Acetylthio)-3-methyl-1-oxopropyl]-1,4-dioxo-7-azaspiro[4.4]nonane-8-carboxylic acid 4,4-Ethylenedioxy-L-proline is reacted with D-3-acetylthio-3-methylpropionyl chloride according to the procedure of Example 1 (e) to yield [7(S), 8S]-7-[3-(acetylthio)-3-methyl-1-oxopropyl]-1,4-dioxo-7-azaspiro[4.4]nonane-8-carboxylic acid.

(b) [7(S),8S]-7-(3-Mercapto-3-methyl-1-oxopropyl)-1,4-dioxo-7-azaspiro[4.4]nonane-8-carboxylic acid The product from part (a) is hydrolyzed with concentrated ammonia according to the procedure of Example 2 to give [7(S),8S]-7-(3-mercapto-3-methyl-1-oxopropyl)-1,4-dioxo-7-azaspiro[4.4]nonane-8-carboxylic acid.

EXAMPLE 38

(S)-1-(3-Mercapto-3-methyl-1-oxopropyl)-4,4-dimethoxy-L-proline (a) (S)-1-[3-(Acetylthio)-3-methyl-1-oxopropyl]-4,4-dimethoxy-L-proline 4,4-Dimethoxy-L-proline is reacted with D-3-acetylthio-3-methylpropionyl chloride according to the procedure of Example 3 (d) to yield (S)-1-[3-(acetylthio)-3-methyl-1-oxopropyl]-4,4-dimethoxy-L-proline.

(b) (S)-1-(3-Mercapto-3-methyl-1-oxopropyl-4,4-dimethoxy-L-proline

The product from part (a) is hydrolyzed with concentrated ammonia according to the procedure of Example 4 to yield (S)-1-(3-mercapto-3-methyl-1-oxopropyl)-4,4-dimethoxy-L-proline.

EXAMPLE 39

1-(3-Mercapto-1-oxopropyl)-4,4-dimethylthio-L-proline (a) 4-Keto-L-proline, hydrobromide To 4.0 g. (0.015 mole) of N-carbobenzyloxy-4-keto-L-proline are added 20 ml. of hydrogen bromide in acetic acid (30–32%). The mixture is frequently swirled over a period of eight minutes. At the end of this period (effervescence has stopped), the yellow-orange solution is layered over with 25° of ether, triturating the gummy product. The ether is discarded and the resulting tacky solid is triturated with fresh ether and finally with 50 ml. of acetonitrile to give 4-keto-L-proline, hydrobromide as a crystalline solid weighing 2.7 g. (85%), m.p. 153°–155° (dec.), $[\alpha]_D^{26}$ −49° (c, 1% in water).

(b) 1-[3-(Acetylthio-1-oxopropyl]-4-oxo-L-proline

A stirred solution of 4.1 g. (0.0195 mole) of 4-keto-L-proline, hydrobromide in 50 ml. of water is cooled to 5° and treated portionwise with solid sodium carbonate (foaming is controlled by adding a few drops of ether)

to pH 8.0 (approx. 2 g. required). Then while continuing stirring and cooling, a solution of 3.5 g. (0.012 mole) of 3-acetylthiopropanoyl chloride in 5 ml. of ethyl acetate is added portionwise by means of a pipette while maintaining the pH at 7.0-8.0 by dropwise addition of 25% (w/v) sodium carbonate solution (about 10 ml.). After about 10 minutes the pH stabilizes at 8.0-8.4. After continued stirring and cooling for a total of 1 hour, the solution is washed with ethyl acetate (2×50 ml.), layered over with 50 ml. of ethyl acetate, stirred, cooled, acidified carefully with concentrated hydrochloric acid to pH 2.0, saturated with sodium chloride, and the layers are separated. The aqueous phase is extracted with additional ethyl acetate (3×50 ml.), the combined organic layers dried (MgSO4) and the solvent evaporated, finally at 0.2 mm. to give 4.8 g. of a yellow-orange glass-like residue. This residue is dissolved in 35 ml. of ethyl acetate and treated with a solution of 3.5 g. of dicyclohexylamine in 5 ml. of ethyl acetate. On seeding and rubbing, crystalline 1-[3-(acetylthio-1-oxopropyl)]-4-oxo-L-proline dicyclohexylamine salt separated, weight after cooling overnight, 2.7 g. (nearly colorless), m.p. 191°-193° (dec.), $[\alpha]_D^{26}$ −24° (c, 1% in CHCl3).

This dicyclohexylamine salt is converted to the free acid using potassium bisulfate as described in Example 1 (e) to give 3.7 g. of 1-[3-(acetylthio)-1-oxopropyl]-4-oxo-L-proline as a pale yellow glass-like solid.

(c) 1-[3-(Acetylthio)-1-oxopropyl]-4,4-dimethylthio-L-proline

The 1-[3-(acetylthio)-1-oxopropyl]-4-oxo-L-proline is reacted with methylthiol according to the procedure of Example 9 (a) to yield 1-[3-(acetylthio)-1-oxopropyl]-4,4-dimethylthio-L-proline.

(d) 1-(3-Mercapto-1-oxopropyl)-4,4-dimethylthio-L-proline

The product from part (a) is hydrolyzed with concentrated ammonia according to the procedure of Example 2 to yield 1-(3-mercapto-1-oxopropyl)-4,4-dimethylthio-L-proline.

EXAMPLE 40

[2(S),3S]-2-(3-Mercapto-2-methyl-B 1-oxopropyl)-8,8-dimethyl-6,10-dioxo-2-azaspiro[4.5]-decane-3-carboxylic acid (a) [2(S), 3S]-2-[3-(Acetylthio)-2-methyl-1-oxopropyl]-8,8-dimethy-6,10-dioxo-2-azaspiro[4.5]decane-3-carboxylic acid Utilizing the procedure of Example 1 but substituting 2,2-dimethyl-1,3-propanediol for the ethylene glycol in part (c), one obtains [2(S), 3S]-2-[3-(acetylthio)-2-methyl-1-oxopropyl]-8,8-dimethyl-6,10-dioxo-2-azaspiro[4.5]decane-3-carboxylic acid.

(b) [2(S), 3S]-2-(3-Mercapto-2-methyl-1-oxopropyl)-8,8-dimethyl-6,10-dioxo-2-azaspiro[4.5]decane-3-carboxylic acid The product from part (a) is hydrolyzed with concentrated ammonia according to the procedure of Example 2 to yield [2(S),3S]-2-(3-mercapto-2-methyl-1-oxopropyl)-8,8-dimethyl-6,10-dioxo-2-azaspiro-[4.5]decane-8-carboxylic acid.

EXAMPLE 41

[7(S),8S]-7-(3-mercapto-2-methyl-1-oxopropyl)-1,4-dioxo-7-azaspiro[4.4]nonane-2-methyl-8-carboxylic acid (a) N-carbobenzyloxy-4,4-(1-methylethylenedioxy)-L-proline, methyl ester A stirred mixture of 8 g. (0.025 mole) of N-carbobenzyloxy-4,4-dimethoxy-L-proline, methyl ester, from Example 3 a, 2.4 g. (0.032 mole) of 1,2-propanediol, 0.4 g. of p-toluenesulfonic acid monohydrate, and 400 ml. of toluene is heated to reflux (110°-112°). The rate of reflux is regulated so that solvent slowly distills by means of a Dean-Stark tube into a graduated cylinder. When 80 ml. of solvent are collected an equal volume of fresh solvent is added to the reaction flask through an addition funnel. This procedure of removing and replacing 80 ml. of solvent is repeated four times during a total reflux period of 1.25 hours.

After standing overnight, the mixture is washed with water. (2×100 ml.), the combined washes are back extracted with 100 ml. of toluene, the combined organic layers are dried (MgSO4), and the solvent is removed on a rotary evaporator, finally at 0.2 mm., to give 8.2 g. (99%) of N-carbobenzyloxy-4,4-(1-methylethylenedioxy)-L-proline, methyl ester as a yellow viscous oil.

(b) N-Carbobenzyloxy-4,4-(1- methylethylenedioxy)-L-proline

The crude methyl ester product from part (a) (8.2 g., 0.025 mole) is dissolved in 80 ml. of methanol, treated dropwise at −1° to 4° with 18 ml. (0.036 mole) of 2 N sodium hydroxide, kept at 0° for one hour, and at room temperature overnight. After removing about half of the solvent on a rotary evaporator, the solution is diluted with 150 ml. of water, washed with 100 ml. of ether (wash discarded), acidified while cooling with 6.3 ml. of 1:1 hydrochloric acid to pH 2, and extracted with ethyl acetate (4×75 ml.). The combined extracts are washed with 50 ml. of saturated sodium chloride, dried (MgSO4), and the solvent evaporated to give 8 g. of a red-orange viscous oil. This oil is dissolved in 50 ml. of acetonitrile, warmed, stirred, and treated with 3.8 g. of 1-adamantanamine. The solid salt rapidly separates. After cooling overnight, the material is filtered, washed with cold acetonitrile and with ether, and dried in vacuo to yield 10.3 g. of crude adamantanamine salt; m.p. 202°-204° (dec.), $[\alpha]_D^{26}$ −13° (c, 1% in methanol). Following trituration with 50 ml. of boiling acetonitrile and cooling, the pale tan solid salt weighed 9.4 g.; m.p. 202°-204° (dec.), $[\alpha]_D^{26}$ −13° (c, 1% in methanol).

The above adamatanamine salt is suspended in 40 ml. of ethyl acetate, stirred, and treated with 1 N hydrochloric acid. When two clear layers are obtained they are separated, the aqueous phase is extracted with additional ethyl acetate (3×40 ml.), the combined organic layers are dried (MgSO4), and the solvent evaporated, finally at 0.2 mm. and 40°, to yield 5.8 g. (72%) of N-carbobenzyloxy-4,4-(1-methylethylenedixoy)-L-proline as a yellow-orange viscous syrup.

(c) 4,4-(1-Methylethylenedioxy)-L-proline

A solution of the above N-carbobenzyloxy-4,4-(1-methylethylenedioxy)-L-proline (5.6 g., 0.017 mole) in 150 ml. of 2:1 methanol-water is treated with 1.6 g. of 5% palladium-carbon catalyst and shaken under 3 atmospheres of hydrogen for five hours. The catalyst is filtered off under nitrogen, washed with methanol, and the combined filtrates evaporated, finally at 0.1–0.2 mm. to give a crystalline residue. The latter is suspended in 200 ml. of methanol and the evaporation repeated. The solid residue is rubbed under ether (evaporation again repeated) to yield 3.0 g. (94%) of pale tan 4,4-(1-methylethylenedioxy)-L-proline; m.p. 219°-221° (dec.); preceded by gradual darkening and sintering; $[\alpha]_D^{25}$ −22° (c, 1% in 1:1 ethanol-water).

(d) [7(S),8S]-7-[3-(Acetylthio)-2-methyl-1-oxopropyl]-1,4-dioxo-7-azaspiro[4.4]nonane-2-methyl-8-carboxylic acid The 4,4-(1-methylethylenedioxy)-L-proline (2.8 g., 0.015 mole) is reacted with 3.0 g. (0.017 mole) of D-3-acetylthio-2-methylpropionyl chloride in 40 ml. of water according to the procedure of Example 1 (e) to give 5.0 g. of a viscous yellow product. The latter is treated with 2.8 g. of dicyclohexylamine in 45 ml. of ethyl acetate to yield 4.2 g. of nearly colorless [7(S),8S]-7-[3-(acetylthio)-2-methyl-1-oxopropyl]-1,4-dioxo-7-azaspiro[4.4]-nonane-2-methyl-8-carboxylic acid, dicyclohexylamine salt; m.p. 170°–172° C. (s, 168° ); $[\alpha]_D^{25}$ −58°; (c, 1% in ethanol). Following crystallization from 12 ml. of acetonitrile, the colorless solid salt weighs 3.85 g. (51%); m.p. 170°–172° (s. 168°); $[\alpha]_D^{25}$ −57°, (c, 1% in ethanol).

Anal. Calc'd. for: $C_{14}H_{21}NO_6S \cdot C_{12}H_{23}N$: C, 60.90; H, 8.65; N, 5.46; S, 6.26. Found: C, 60.93; H, 8.72; N, 5.43; S, 6.35.

The dicyclohexylamine salt is converted to the free acid by suspending 3.8 g. in ethyl acetate and treating with 45 ml. of 10% potassium bisulfate and stirring until two layers are obtained. After separating, the aqueous phase is extracted with ethyl acetate (4×40 ml.), the organic layers are combined, dried (MgSO₄) and the solvent evaporated to give 2.5 g. (51%) of colorless solid [7(S),8S]-7-[3-(acetylthio)-2-methyl-1-oxopropyl]-1,4-dioxo-7-azaspiro[4.4]nonane-2-methyl-8-carboxylic acid, m.p. 65°–68° (s. 48°); $[\alpha]_D^{25}$ −100°, (c, 1% in ethanol).

(e) [7(S), 8S]-7-(3-mercapto-2-methyl-1-oxopropyl)-1,4-dioxo-7-azaspiro[4.4]nonane-2-methyl-8-carboxylic acid The product from part (d) is hydrolyzed with concentrated ammonia according to the procedure of Example 2 to give 2.05 g. of [7(S),8S]-7-(3-mercapto-2-methyl-1-oxopropyl)-1,4-dioxo-7-azaspiro[4.4]nonane-2-methyl-8-carboxylic acid as a viscous colorless oil $[\alpha]_D^{25}$ −57°(c, 1% in ethanol).

EXAMPLES 42–75

Following the procedure of Example 41 the dimethoxy substituted compound of Column I (or its alkyl ester) is treated with the diol or dithiol of Column II to yield the spiro intermediate of column III. Removal of the N-protecting group (and the alkyl ester group) and acylation with the acyl chloride of Column IV yields the product of Column V which can then be hydrolyzed to the product of Column VI.

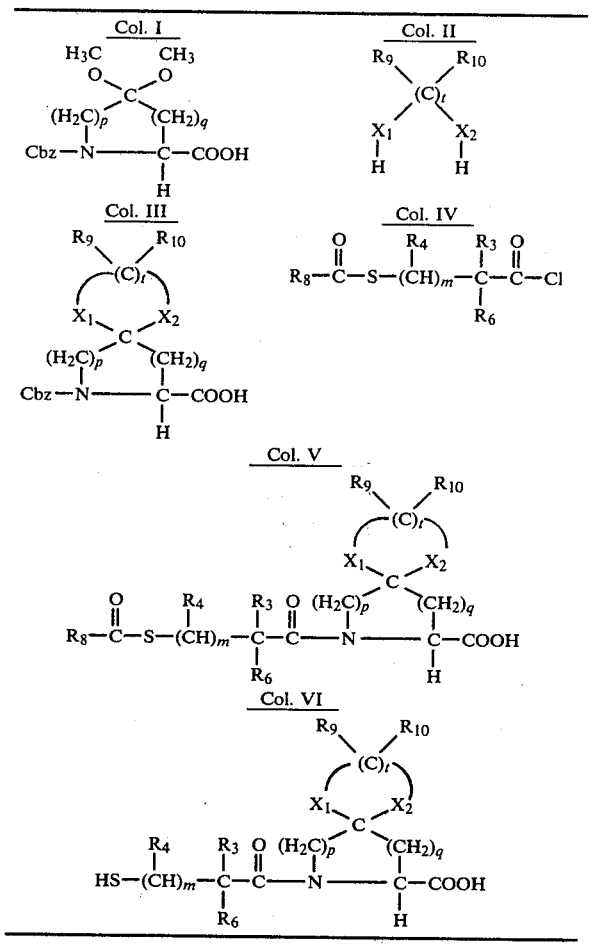

| Example | p | q | $\begin{array}{c} R_9 \quad R_{10} \\ (C)_t \\ X_1 \quad X_2 \\ H \quad\quad H \end{array}$ | $R_3$ | $R_6$ | $R_4$ | m | $R_8$ |
|---|---|---|---|---|---|---|---|---|
| 42 | 1 | 1 | H₂C—C(CH₃)(O H)(O H)(CH₃) | CH₃ | H | H | 1 | CH₃ |
| 43 | 1 | 1 | H₃C, CH₃ / C / H₂C CH₂ / S S / H H | CH₃ | H | H | 1 | CH₃ |
| 44 | 1 | 1 | H₂C—CH(CH₂OH)(O H)(O H) | CH₃ | H | H | 1 | CH₃ |

-continued

| | | | R9, R10, X1(H), X2(H) on (C)t structure | | | | | |
|---|---|---|---|---|---|---|---|---|
| Example | p | q | structure | $R_3$ | $R_6$ | $R_4$ | m | $R_8$ |
| 45 | 1 | 1 | $H_3C-CH(OH)-CH(OH)-CH_3$ | $CH_3$ | H | H | 1 | $CH_3$ |
| 46 | 1 | 1 | $(H_5C_2)_2C(CH_2OH)_2$ | $CH_3$ | H | H | 1 | phenyl |
| 47 | 1 | 1 | $H_2C(OH)-CH_2(OH)$ | H | H | H | 1 | 2-thienyl-$CH_2-$ |
| 48 | 1 | 1 | $H_2C(SH)-CH_2(SH)$ | $CF_3$ | H | H | 1 | 4-Cl-phenyl |
| 49 | 1 | 1 | $H_2C(OH)-CH_2(SH)$ | H | H | H | H | 4-$H_3CO$-phenyl-$CH_2-$ |
| 50 | 1 | 1 | $H_2C(OH)-C(OH)(H)-C_2H_5$ | $CH_3$ | $CH_3$ | H | 1 | cyclohexyl |
| 51 | 1 | 1 | $H_2C(OH)-CH(CF_3)-CH_2(OH)$ | H | H | — | zero | $C_2H_5$ |
| 52 | 1 | 1 | $H_2C(OH)-C(OH)(H)-CH_2Cl$ | H | H | H | 2 | phenyl |
| 53 | 1 | 1 | $H_2C(OH)-C(OH)(H)-CH_2-phenyl$ | $CH_3$ | H | H | 1 | $CH_3$ |
| 54 | 1 | 1 | $H_2C(SH)-C(SH)(H)-CH_2-2-thienyl$ | $CH_3$ | H | H | 1 | phenyl |
| 55 | 1 | 1 | $H_2C(OH)-C(OH)(H)(CH_2-)-CH_2-2-furyl$ | $CH_3$ | H | H | 1 | 4-pyridyl |
| 56 | 1 | 1 | $H_2C(SH)-C(SH)(H)(CH_2-)-CH_2-(3-Cl-phenyl)$ | $CH_3$ | H | H | 1 | $CH_3$ |
| 57 | 1 | 1 | $H_2C(OH)-CH(OH)-(CH_2)_2-(4-SCH_3-phenyl)$ | $CH_3$ | H | — | zero | 2-furyl |

-continued

| Example | p | q | (structure with R9,R10,X1,X2,(C)t, bottom Hs) | R3 | R6 | R4 | m | R8 |
|---|---|---|---|---|---|---|---|---|
| 58 | 1 | 1 | p-OCH3-C6H4-CH2-CH(CH2OH)(CH2OH) | CH3 | H | H | 1 | H3C-C6H4- |
| 59 | 1 | 1 | H2C(OH)-CH(OH)-CH2-C6H4-CH3 | H | H | H | 2 | CH3 |
| 60 | 1 | 1 | H2C(SH)-CH(SH)-CH2-(4-piperidyl) | CH3 | H | H | 1 | F-C6H4-CH2 |
| 61 | 2 | 1 | H2C(OH)-CH2(OH) | CH3 | H | H | 1 | CH3 |
| 62 | 1 | 2 | H2C(OH)-CH2(OH) | CH3 | H | H | 1 | CH3 |
| 63 | 1 | 2 | H2C(SH)-CH2(SH) | CH3 | H | H | 1 | C6H5 |
| 64 | 1 | 2 | H2C(OH)-CH(CH2OH)- | CH3 | H | H | 1 | H3CO-C6H4-CH2- |
| 65 | 2 | 1 | H2C(SH)-CH(CH2SH)- | CF3 | H | H | 1 | CH3 |
| 66 | 2 | 1 | H2C(OH)-CH2(SH) | H | H | H | 1 | 2-thienyl |
| 67 | 2 | 1 | H2C(OH)-CH(OH)-CH2-C6H5 | CH3 | H | H | 1 | 2-furyl-CH2 |
| 68 | 1 | 2 | p-OCH3-C6H4-CH2-CH(CH2OH)(CH2OH) | H | H | H | 2 | C2H5 |
| 69 | 1 | 2 | (H3C)(H3C)C(CH2OH)(CH2OH) | H | H | — | zero | 3-Cl-C6H4- |
| 70 | 1 | 1 | H3C-HC(OH)-CH(OH)-CH3 | SCH3 | H | H | 1 | CH3 |
| 71 | 2 | 1 | H2C(OH)-CH(OH)-CF3 | CH3 | H | H | 1 | CH3 |
| 72 | 2 | 1 | H2C(SH)-CH(SH)-CH2-(2-thienyl) | CH3 | H | H | 1 | CH3 |

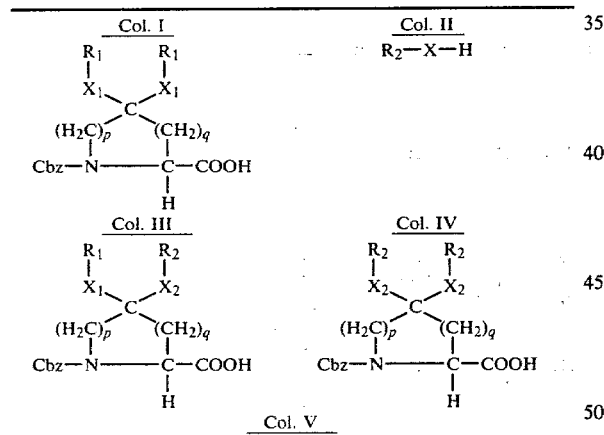

EXAMPLES 75–124

Following the procedure of Example 41 the disubstituted compound of Column I (or its alkyl ester) is treated with a molar equivalent of the alcohol or thiol of Column II to yield the compound shown in Column III. Alternatively, by treating the dimethoxy substituted compound of formula I (or its alkyl ester) with a molar excess of the alcohol or thiol of Column II one obtains the disubstituted compound of Column IV. Removal of the N-protecting group (and the alkyl ester group) from the intermediate of either Column III or IV followed by acylation with the acid chloride of Column V yields the product of Columns VI and VII, respectively. These compounds can then be hydrolyzed to the products of Columns VIII and IX, respectively,

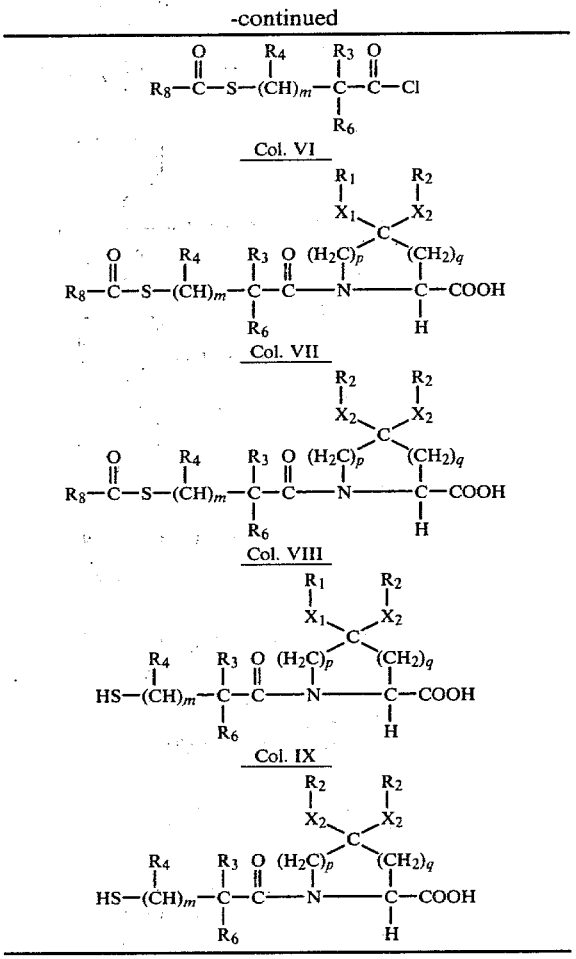

| Example | p | q | $X_1$—$R_1$ | $X_2$—$R_2$ | $R_3$ | $R_6$ | $R_4$ | m | $R_8$ |
|---|---|---|---|---|---|---|---|---|---|
| 75 | 1 | 1 | —O—$CH_3$ | —S—$CH_3$ | —$CH_3$ | H | H | 1 | phenyl |
| 76 | 1 | 1 | —O—$CH_3$ | —S—$C_2H_5$ | —$CH_3$ | H | H | 1 | $H_3CO$—phenyl—$CH_2$— |
| 77 | 1 | 1 | —O—$CH_3$ | —O—i-$C_3H_7$ | H | H | H | 2 | $CH_3$ |
| 78 | 1 | 1 | —O—$CH_3$ | —O—t-$C_4H_9$ | —$CH_3$ | —$CH_3$ | H | 1 | thienyl |

-continued

| Example | p | q | X₁—R₁ | X₂—R₂ | R₃ | R₆ | R₄ | m | R₈ |
|---|---|---|---|---|---|---|---|---|---|
| 79 | 1 | 1 | —O—CH₃ | —O—CH₂—C₆H₅ | —CH₃ | H | H | 1 | CH₃ |
| 80 | 1 | 1 | —O—CH₃ | —O—CH₂—C₆H₄—CH₃ | H | H | — | zero | furyl |
| 81 | 1 | 1 | —O—CH₃ | —O—CH₂—C₆H₄—OCH₃ | —CH₃ | H | 1 | 1 | CH₃ |
| 82 | 1 | 1 | —O—CH₃ | —O—(CH₂)₂—C₆H₄—Cl | H | H | H | 1 | piperidinyl |
| 83 | 1 | 1 | —O—CH₃ | —O—CH₂—C₆H₄—CF₃ | —CH₃ | H | H | 1 | cyclopentyl |
| 84 | 1 | 1 | —O—CH₃ | —O—(CH₂)₃—C₆H₄—S—CH₃ | H | H | — | zero | thienyl-CH₂— |
| 85 | 1 | 1 | —O—CH₃ | —O—CH₂—(thienyl) | —CH₃ | H | H | 1 | furyl-CH₂ |
| 86 | 1 | 1 | —O—CH₃ | —O—(CH₂)₂—(thienyl) | —SCH₃ | H | H | 1 | C₂H₅ |
| 87 | 1 | 1 | —O—CH₃ | —O—CH₂—(furyl) | —CH₃ | H | H | 1 | C₆H₅—(CH₂)₂ |
| 88 | 1 | 1 | —O—CH₃ | —O—CH₂—(furyl) | —C₂H₅ | H | H | 1 | CH₃ |
| 89 | 1 | 1 | —O—CH₃ | —O—CH₂—(pyridyl) | H | H | — | zero | C₆H₄—CH₃ |
| 90 | 1 | 1 | —O—CH₃ | —O—CH₂—(piperidyl) | —CH₃ | H | H | 1 | CH₃ |
| 91 | 1 | 1 | —O—CH₃ | —O—CH₂CCl₃ | —CH₃ | H | H | 1 | CH₃ |
| 92 | 1 | 1 | —O—C₂H₅ | —O—CH₂CF₃ | H | H | CH₃ | 1 | CH₃ |
| 93 | 1 | 1 | —O—CH₃ | —O—CH₂Br | —CH₃ | —CH₃ | H | 1 | C₆H₅ |
| 94 | 1 | 1 | —O—CH₃ | —O—CH₂—OH | —CH₃ | H | H | 1 | CH₃ |
| 95 | 1 | 1 | —O—CH₃ | —O—CH₂CH₂OH | H | H | H | 2 | C₆H₅ |
| 96 | 1 | 1 | —O—C₂H₅ | —O—CH=CH₂ | —CH₃ | H | H | 1 | C₂H₅ |
| 97 | 1 | 1 | —O—CH₃ | —O—CH₂CH=CH₂ | H | H | — | zero | CH₃ |
| 98 | 1 | 1 | —O—CH₃ | —O—CH₂C≡CH | H | H | H | 1 | thienyl |
| 99 | 1 | 1 | —O—CH₃ | —O—cyclohexyl | —CH₃ | H | H | 1 | furyl |
| 100 | 1 | 1 | —O—CH₃ | —S—t-C₄H₉ | H | H | H | 1 | C₆H₅ |
| 101 | 1 | 1 | —O—C₂H₅ | —S—CH₂—C₆H₅ | —CH₃ | H | H | 1 | CH₃ |
| 102 | 1 | 1 | —O—CH₃ | —S—(CH₂)₂—C₆H₄—OCH₃ | H | H | H | 2 | H₃CO—C₆H₄—CH₂— |

-continued

| Example | p | q | X₁—R₁ | X₂—R₂ | R₃ | R₆ | R₄ | m | R₈ |
|---|---|---|---|---|---|---|---|---|---|
| 103 | 1 | 1 | —O—CH₃ | —S—CH₂—(C₆H₄)—Cl | CF₃ | H | H | 1 | CH₃ |
| 104 | 1 | 1 | —O—C₂H₅ | —S—CH₂—(C₆H₄)(CF₃) | H | H | — | zero | CH₃ |
| 105 | 1 | 1 | —O—CH₃ | —S—CH₂-(thienyl) | —CH₃ | H | H | 1 | CH₃ |
| 106 | 1 | 1 | —O—CH₃ | —S—(CH₂)₂-(thienyl) | —SCH₃ | H | H | 1 | CH₃ |
| 107 | 1 | 1 | —O—CH₃ | —S—CH₂-(furyl) | —CF₃ | H | H | 1 | —CH₂—C₆H₅ |
| 108 | 1 | 1 | —O—CH₃ | —S—CH₂-(pyridyl) | H | H | H | 2 | —CH₂-(thienyl) |
| 109 | 1 | 1 | —O—C₂H₅ | —S—C₆H₅ | —CH₃ | H | H | 1 | —(CH₂)₂—C₆H₅ |
| 110 | 1 | 1 | —O—CH₃ | —S—CH₂—CH=CH₂ | H | H | H | 1 | CH₃ |
| 111 | 1 | 1 | —O—CH₃ | —S—CH₂—C≡CH | H | H | — | zero | CH₃ |
| 112 | 2 | 1 | —O—CH₃ | —O—CH₂—C₆H₅ | —CH₃ | H | H | 1 | CH₃ |
| 113 | 1 | 2 | —O—CH₃ | —O—(CH₂)₂—C₆H₅ | —CH₃ | H | H | 1 | CH₃ |
| 114 | 1 | 2 | —O—CH₃ | —O—CH₂—(C₆H₄)—SCH₃ | H | H | H | 2 | C₂H₅ |
| 115 | 2 | 1 | —O—CH₃ | —O—CH₂-(thienyl) | —CH₃ | H | H | 1 | —C₆H₅ |
| 116 | 2 | 1 | —OCH₃ | —O—CH₂-(furyl) | —CF₃ | H | H | 1 | CH₃ |
| 117 | 1 | 2 | —O—CH₃ | —S—CH₂—(C₆H₄)—CF₃ | H | H | H | 2 | CH₃ |
| 118 | 1 | 3 | —O—CH₃ | —S—CH₂—(C₆H₄)—OCH₃ | —CH₃ | H | H | 1 | CH₃ |
| 119 | 1 | 2 | —O—CH₃ | —S—(CH₂)₂-(thienyl) | H | H | — | zero | CH₃ |
| 120 | 1 | 2 | —O—CH₃ | —O—CH₂CCl₃ | H | H | H | 1 | CH₃ |
| 121 | 2 | 1 | —O—CH₃ | —O—CF₃ | —CH₃ | H | H | 1 | CH₃ |
| 122 | 2 | 1 | —O—CH₃ | —O—CH₂OH | —CH₃ | H | H | 1 | —C₆H₅ |
| 123 | 1 | 2 | —O—CH₃ | —O—CH₂—CH=CH₂ | —CH₃ | H | H | 1 | CH₃ |
| 124 | 2 | 1 | —O—CH₃ | —S—CF₃ | —CH₃ | H | H | 1 | CH₃ |

EXAMPLE 125

(S,S,S,S)-7,7'-[Dithiobis(2-methyl-1-oxo-3,1-propanediyl)]bis[1,4-dioxa-7-azaspiro[4.4]nonane-8-carboxylic acid]

[7(S),8S]-7-(3-Mercapto-2-methyl-1-oxopropyl)-1,4-dioxo-7-azaspiro[4.4]nonane-8-carboxylic acid (3.0 g., 0.0109 mole) from Example 2 is dissolved in 80 ml. of water and the pH is adjusted to 6.5 with 1 N sodium hydroxide. To this stirred solution is added dropwise a total of 11 ml. of 0.5 M iodine solution in 95% ethanol (6.34 g. iodine/50 ml. solution) while maintaining the pH at 5.5 to 6.5 with 1 N sodium hydroxide. After 15 minutes, a trace of excess iodine is removed with dilute sodium thiosulfate and the solution is concentrated to approximately 50 ml., cooled and acidified with 1:1 hydrochloric acid. Methylene chloride (30 ml.) is added and the mixture is saturated with sodium chloride, stirred, and the layers separated. The aqueous phase is extracted with additional methylene chloride (3×20 ml.), and combined organic layers dried (MgSO4), and the solvent evaporated, finally at 0.2 mm. The brittle residue is rubbed under ether and the evaporation repeated to give 2.8 g. of a pale yellow solid residue. The material is redissolved in 50 ml. of methylene chloride, washed with water (3×10 ml.), the combined aqueous layers back-extracted with 20 ml. of methylene chloride, and the combined layers dried (MgSO4). Evaporation and trituration with ether as above yields 2.2 g. (73%) of cream-colored amorphous solid (S,S,S,S)-7,7'-[dithiobis(2-methyl-1-oxo-3,1-propanediyl)]bis[1,4-dioxo-7-azaspiro[4.4]nonane-8-carboxylic acid]; m.p. 61°–63° (foaming), (s. 50°), $[\alpha]_D^{26} -92°$, (c, 1% in ethanol).

Anal. Calc'd. for $C_{22}H_{32}N_2O_{10}S \cdot H_2O$: C, 46.63; H. 6.05; N, 4.94; S, 11.31. Found: C, 46.52; H, 6.29; N, 4.63; S, 10.96.

EXAMPLE 126

(S,S,S,S)-7,7'-[Dithiobis(2-methyl-oxo-3,1-propanediyl)]bis[7-aza-1,4-dithiaspiro[4.4]nonane-8-carboxylic acid]

[7(S),8S]-7-(3-Mercapto-2-methyl-1-oxopropyl)-7-aza-1,4-dithiaspiro[4.4]nonane-8-carboxylic acid from Example 10 is reacted with iodine according to the procedure of Example 125 to yield (S,S,S,S)-7,7'-[dithiobis(2-methyl-1-oxo-3,1-propanediyl)]bis-[7-aza-1,4-dithiaspiro[4.4]nonane-8-carboxylic acid].

EXAMPLE 127

(S,S,S,S)-1,1'-[Dithiobis(2-methyl-1-oxo-3,1-propanediyl)]bis[4,4-dimethoxy-L-proline]

(S)-1-(3-Mercapto-2-methyl-1-oxopropyl)-4,4-dimethoxy-L-proline from Example 4 is reacted with iodine according to the procedure of Example 125 to yield (S,S,S,S)-1,1'-[dithiobis(2-methyl-1-oxo-3,1-propanediyl)]bis[4,4-dimethoxy-L-proline].

EXAMPLE 128

[7(S),8(S)]-7-[3-(Acetylthio)-2-methyl-1-oxopropyl]-1,4-dioxo-7-azaspiro[4.4]nonane-8-carboxylic acid, methyl ester A solution of the product of Example 1 in ether is treated with a slight excess of diazomethane. After standing at room temperature for two hours, the solvent is evaporated to give [7(S),8S]-7-[3-(acetylthio)-2-methyl-1-oxopropyl]-1,4-dioxo-7-azaspiro[4.4]nonane-8-carboxylic acid, methyl ester.

EXAMPLE 129

[7(S),8S]-7-(3-Mercapto-2-methyl-1-oxopropyl)-1,4-dioxo-7-azaspiro[4.4]nonane-8-carboxylic acid, methyl ester The product from Example 128 is hydrolyzed with concentrated ammonia according to the procedure of Example 2 to yield [7(S),8S]-7-(3-mercapto-2-methyl-1-oxopropyl)-1,4-dioxo-7-azaspiro[4.4]nonane-8-carboxylic acid, methyl ester.

EXAMPLE 130

(S)-1-[3-(Acetylthio)-2-methyl-1-oxopropyl]-4,4-dimethoxy-L-proline, methyl ester A solution of the product from Example 3 in ether is treated with a slight excess of diazomethane. After standing at room temperature, the solvent is evaporated to give (S)-1-[3-(acetylthio)-2-methyl-1-oxopropyl]-4,4-dimethoxy-L-proline, methyl ester.

EXAMPLE 131

(S)-1-(3-Mercapto-2-methyl-1-oxopropyl)-4,4-dimethoxy-L-proline, methyl ester

The product from Example 130 is hydrolyzed with concentrated ammonia according to the procedure of Example 4 to yield (S)-1-(3-mercapto-2-methyl-1-oxopropyl)-4,4-dimethoxy-L-proline, methyl ester.

EXAMPLE 132

[7(S),8S]-7-(3-Mercapto-2-methyl-1-oxopropyl)-1,4-dioxo-7-azaspiro[4.4]nonane-8-carboxylic acid, sodium salt A solution of 1.0 g. of the product of Example 2 is dissolved in 10 ml. of water and treated with one equivalent of sodium bicarbonate. The solution is freeze-dried to give [7(S),8S]-7-(3-mercpato-2-methyl-1-oxopropyl)-1,4-dioxo-7-azaspiro[4.4]nonane-8-carboxylic acid, sodium salt.

In a similar manner, by employing potassium bicarbonate the corresponding potassium salt is obtained.

EXAMPLE 133

(S)-1-(3-Mercapto-2-methyl-1-oxopropyl)-4,4-dimethoxy-L-proline, sodium salt

A solution of 1.0 g. of the product of Example 4 is dissolved in 10 ml. of water and treated with one equivalent of sodium bicarbonate. The solution is freeze-dried to give (S)-1-(3-mercapto-2-methyl-1-oxopropyl)-4,4-dimethoxy-L-proline, sodium salt.

In a similar manner, by employing potassium bicarbonate the corresponding potassium salt is obtained.

EXAMPLE 134

1000 tablets each containing the following ingredients:

| | |
|---|---|
| [7(S),8S]-7-(3-Mercapto-2-methyl-1-oxopropyl)-1,4-dioxo-7-azaspiro[4.4]nonane-8-carboxylic acid | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared (from sufficient bulk quantities) by mixing the [7(S),8S]-7-(3-mercapto-2-methyl-1-oxopropyl)-1,4-dioxo-7-azaspiro[4.4]nonane-8-carboxylic acid and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

EXAMPLE 135

Tablets each containing 100 mg. of (S)-1-(3-mercapto-2-methyl-1-oxopropyl)-4,4-dimethoxy-L-proline are produced as described in Example 134.

EXAMPLE 136

1000 tablets each containing 50 mg. of [7(S),8S]-7-(3-mercapto-2-methyl-1-oxopropyl)-1,4-dioxo-7-azaspiro[4.4]nonane-8-carboxylic acid are produced from the following ingredients

| | |
|---|---|
| [7(S),8S]-7-(3-mercapto-2-methyl-1-oxopropyl)-1,4-dioxo-7-azaspiro[4.4]nonane-8-carboxylic acid | 50 g. |
| Lactose | 100 g. |
| Avicel | 150 g. |
| Corn starch | 50 g. |
| Magnesium stearate | 5 g. |

The [7(S),8S]-7-[3-mercapto-2-methyl-1-oxopropyl]-1,4-dioxo-7-azaspiro[4.4]nonane-8-carboxylic acid, lactose, and Avicel are admixed, then blended with the corn starch. Magnesium stearate is added. The dry mixture is compressed in a tablet press to form 1000 355 mg. tablets each containing 50 mg. of active ingredient. The tablets are coated with a solution of Methocel E 15 (methyl cellulose) including as a color a lake containing yellow #6.

EXAMPLE 137

Tablets each containing 50 mg. of (S)-1-(3-mercapto-2-methyl-1-oxopropyl)-4,4-dimethoxy-L-proline are produced as described in Example 136.

EXAMPLE 138

Two piece #1 gelatin capsules each containing 100 mg. of [7(S),8S]-7-(3-mercapto-2-methyl-1-oxopropyl)-1,4-dioxo-7-azaspiro[4.4]nonane-8-carboxylic acid, sodium salt, are filled with a mixture of the following ingredients:

| | |
|---|---|
| [7(S),8S]-7-(3-mercapto-2-methyl-1-oxopropyl)-1,4-dioxo-7-azaspiro[4.4]nonane-8-carboxylic acid, sodium salt | 100 mg. |
| Magnesium stearate | 7 mg. |
| Lactose | 193 mg. |

EXAMPLE 139

Gelatin capsules containing 100 mg. of (S)-1-(3-mercapto-2-methyl-1-oxopropyl)-4,4-dimethoxy-L-proline, sodium salt are produced as described in Example 138.

EXAMPLE 140

An injectable solution is produced as follows:

| | |
|---|---|
| [7(S),8S]-7-(3-Mercapto-2-methyl-1-oxopropyl)-1,4-dioxo-7-azaspiro[4.4]nonane-8-carboxylic acid | 500 g. |
| Methyl paraben | 5 g. |
| Propyl paraben | 1 g. |
| Sodium chloride | 25 g. |
| Water for injection qs. | 5 l |

The active substance, preservatives and sodium chloride are dissolved in 3 liters of water and then the volume is brought up to 5 liters. The solution is filtered through a sterile filter and aseptically filled into presterilized vials which are then closed with presterilized rubber closures. Each vial contains 5 ml. of solution in a concentration of 100 mg. of active ingredient per ml. of solution for injection.

EXAMPLE 141

An injectable solution containing (S)-1-(3-mercapto-2-methyl-1-oxopropyl)-4,4-dimethoxy-L-proline is prepared as described in Example 140.

EXAMPLE 142

6000 tablets each containing the following ingredients:

| | | |
|---|---|---|
| [7(S),8S]-7-mercapto-2-methyl-1-oxopropyl)-1,4-dioxo-7-azaspiro-[4.4]nonane-8-carboxylic acid | 100 | mg. |
| Avicel (microcrystalline cellulose) | 100 | mg. |
| Hydrochlorothiazide | 12.5 | mg. |
| Lactose U.S.P. | 113 | mg. |
| Corn starch U.S.P. | 17.5 | mg. |
| Stearic acid U.S.P. | 7 | mg. |
| | 350 | mg. | are produced from sufficient bulk quantities by slugging the [7(S),8S]-7-(3-mercapto-2-methyl-1-oxopropyl)-1,4-dioxo-7-azaspiro[4.4]nonane-8-carboxylic acid, aricel and a portion of the stearic acid. The slugs are ground and passed through a #2 screen, then mixed with the hydrochlorothiazide, lactose, corn starch and remainder of the stearic acid. The mixture is compressed into 350 mg. capsule shaped tablets in a tablet press. The tablets are scored for dividing in half.

EXAMPLE 143

Tablets each containing (S)-1-(3-mercapto-2-methyl-1-oxopropyl)-4,4-dimethoxy-L-proline and hydrochlorothiazide can be prepared as described in Example 142.

The product of Examples 1, 3 and 6 to 133 can also be formulated according to the procedures of Examples 134–143.

What is claimed is:

1. A compound of the formula $$R_5-S-(CH)_m-\underset{R_6}{\underset{|}{C}}-\underset{\|}{\overset{O}{C}}-N\underset{(H_2C)_p}{\overset{R_3}{\diagup}}\underset{(CH_2)_q}{\overset{R_1}{\diagdown}}\underset{X_2}{\overset{R_2}{\diagdown}}C\underset{H}{\overset{|}{-}}COOR$$

or a pharmaceutically acceptable salt thereof wherein

R is hydrogen or lower alkyl;

$R_1$ and $R_2$ are independently selected from the group consisting of lower alkyl, lower alkenyl, lower alkynyl, cycloalkyl, halo substituted lower alkyl, hydroxy substituted lower alkyl, $-(CH_2)_n-\underset{R_7}{\diagdown}$ , $-(CH_2)_n-\underset{X_3}{\diagdown}$ , and -continued

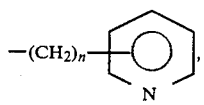

or $R_1$ and $R_2$ join together in a polymethylene chain of the formula

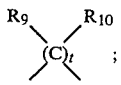

$X_1$, $X_2$ and $X_3$ are independently selected from the group consisting of oxygen and sulfur;

$R_3$ and $R_4$ are independently selected from the group consisting of hydrogen, lower alkyl, lower alkylthio, $-(CH_2)_n-SH$, and halo substituted lower alkyl;

$R_6$ is hydrogen or lower alkyl provided that $R_6$ is lower alkyl only when $R_3$ is lower alkyl;

m is zero, one or two;

n is one, two or three;

p and q are each one or two provided that both are not two;

t is two or three;

$R_7$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

$R_9$ and $R_{10}$ are both hydrogen, both lower alkyl, or one is hydrogen and the other is lower alkyl, halo substituted lower alkyl, hydroxy substituted lower alkyl,

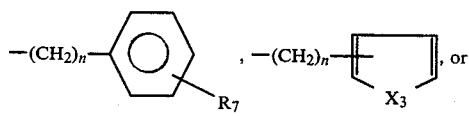

$R_5$ is hydrogen,

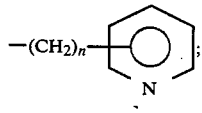

p-methoxybenzyloxycarbonyl, trityl, t-butoxycarbonyl, or provided neither $R_3$ nor $R_4$ is $-(CH_2)_n-SH$

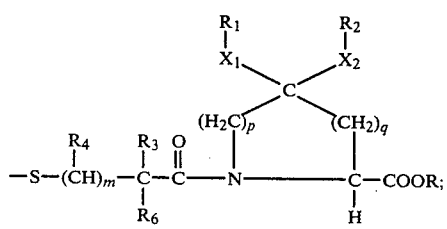

and $R_8$ is lower alkyl, halo substituted lower alkyl, $-(CH_2)_r$-cycloalkyl,

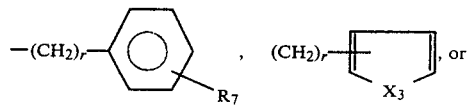

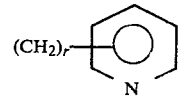

wherein r is zero, one, two or three and $R_7$ and $X_3$ are as defined above.

2. The compound of claim 1 wherein p is two and q is one.

3. The compound of claim 1 wherein p is one and q is two.

4. The compound of claim 1 wherein p and q are both one.

5. The compound of claim 4 wherein $X_1$ and $X_2$ are independently selected from the group consisting of oxygen or sulfur; R is hydrogen or lower alkyl; $R_1$ and $R_2$ each is lower alkyl of 1 to 4 carbons or form two joined methylene groups; $R_3$ and $R_4$ each is hydrogen or lower alkyl of 1 to 4 carbons; $R_5$ is hydrogen, lower alkanoyl of 1 to 4 carbons, or benzoyl; $R_6$ is hydrogen, and m is zero or one.

6. The compound of claim 4 wherein $X_1$ and $X_2$ each is oxygen; R, $R_4$, $R_5$ and $R_6$ each is hydrogen; $R_1$ and $R_2$ each is lower alkyl of 1 to 4 carbons or $R_1$ and $R_2$ each is methylene and join to complete the ethylenedioxy ring; $R_3$ is methyl; and m is one.

7. The compound of claim 4 wherein $X_1$-$R_1$ and $X_2$-$R_2$ complete an ethylenedioxy ring.

8. A compound of the formula

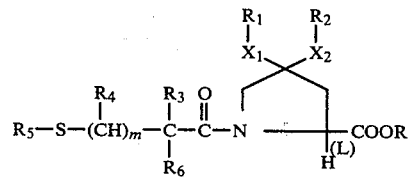

or a pharmaceutically acceptable salt thereof, wherein R is hydrogen or lower alkyl;

$R_1$ and $R_2$ are independently selected from the group consisting of lower alkyl, lower alkenyl, lower alkynyl, cycloalkyl, halo substituted lower alkyl, hydroxy substituted lower alkyl

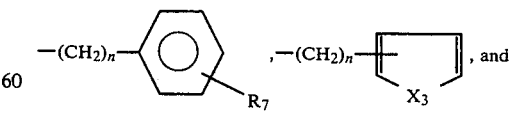

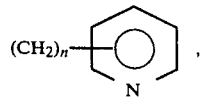

or $R_1$ and $R_2$ join together in a polymethylene chain of the formula

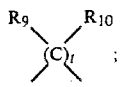

$X_1$, $X_2$ and $X_3$ are independently selected from the group consisting of oxygen and sulfur;

$R_3$ and $R_4$ are independently selected from the group consisting of hydrogen, lower alkyl, lower alkylthio, —(CH$_2$)$_n$—SH, and halo substituted lower alkyl;

$R_6$ is hydrogen or lower alkyl provided that $R_6$ is lower alkyl only when $R_3$ is lower alkyl;

m is zero, one or two;

n is one, two, or three;

t is two or three;

$R_7$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

$R_9$ and $R_{10}$ are both hydrogen, both lower alkyl, or one is hydrogen and the other is lower alkyl, halo substituted lower alkyl, hydroxy substituted lower alkyl,

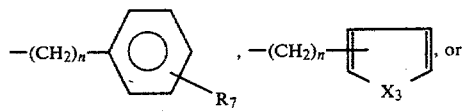

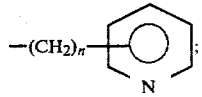

$R_5$ is hydrogen,

p-methoxybenzyloxycarbonyl, trityl, t-butoxycarbonyl, or provided that neither $R_3$ nor $R_4$ is —(CH$_2$)$_n$—SH

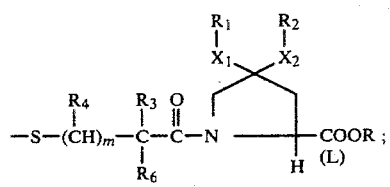

and $R_8$ is lower alkyl, halo substituted lower alkyl, —(CH$_2$)$_r$-cycloalkyl,

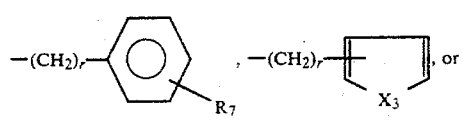

-continued

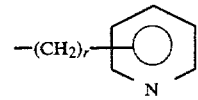

wherein r is zero, one, two or three and $R_7$ and $X_3$ are as defined above.

9. The compound of claim 8 wherein R is hydrogen; $R_4$ is hydrogen; $R_3$ and $R_6$ are both lower alkyl of 1 to 4 carbons or $R_6$ is hydrogen and $R_3$ is hydrogen, lower alkyl of 1 to 4 carbons, trifluoromethyl, methylthio, or mercaptomethyl; $R_5$ is hydrogen, lower alkanoyl of 1 to 4 carbons, or benzoyl; $X_1$ and $X_2$ are oxygen or sulfur; $R_1$ and $R_2$ are lower alkyl of 1 to 4 carbons,

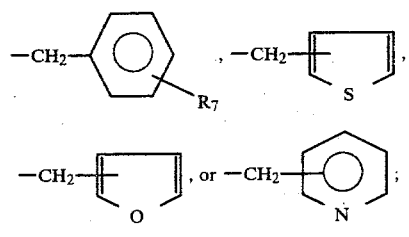

m is zero or one; and $R_7$ is hydrogen, methyl, methoxy, methylthio, chloro, bromo, fluoro, trifluoromethyl, or hydroxy.

10. The compound of claim 9 wherein R is hydrogen; $R_4$ is hydrogen; $R_3$ and $R_6$ are both methyl or $R_6$ is hydrogen and $R_3$ is hydrogen, methyl, trifluoromethyl, methylthio, or mercaptomethyl; $R_5$ is hydrogen, acetyl, or benzoyl; $X_1$ and $X_2$ are the same; $R_1$ and $R_2$ are methyl, ethyl,

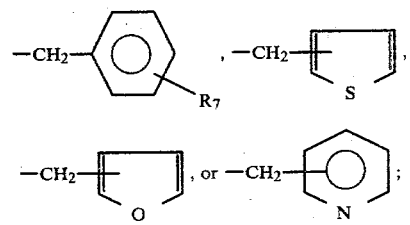

m is zero or one; and $R_7$ is hydrogen, methyl, methoxy, methylthio, chloro, bromo, fluoro, trifluoromethyl, or hydroxy.

11. The compound of claim 10 wherein R, $R_4$, $R_5$, and $R_6$ are hydrogen; $R_3$ is methyl; m is one; and $R_1$ and $R_2$ are both methyl or ethyl.

12. The compound of claim 11 wherein $X_1$ and $X_2$ are both oxygen.

13. The compound of claim 12, (S)-1-(3-mercapto-2-methyl-1-oxopropyl)-4,4-dimethoxy-L-proline.

14. The compound of claim 12, (S)-1-(3-mercapto-2-methyl-1-oxopropyl)-4,4-diethoxy-L-proline.

15. The compound of claim 8 wherein R is hydrogen; $R_4$ is hydrogen; $R_3$ and $R_6$ are both lower alkyl of 1 to 4 carbons or $R_6$ is hydrogen and $R_3$ is hydrogen, lower alkyl of 1 to 4 carbons, trifluoromethyl, methylthio, or mercaptomethyl; $R_5$ is hydrogen, lower alkanoyl of 1 to 4 carbons, or benzoyl; $X_1$-$R_1$ and $X_2$-$R_2$ join to form

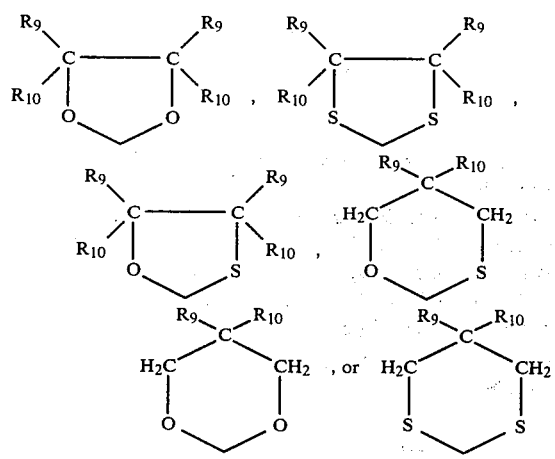

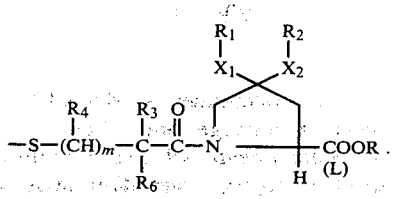

R9 and R10 are both hydrogen or both lower alkyl of 1 to 4 carbons; or R9 is hydrogen and R10 is lower alkyl of 1 to 4 carbons, hydroxy substituted lower alkyl of 1 to 4 carbons, or halogen substituted lower alkyl of 1 to 4 carbons; m is zero or one.

16. The compound of claim 15 wherein R9 and R10 are both hydrogen or R9 is hydrogen and R10 is methyl, hydroxymethyl, or trifluoromethyl.

17. The compound of claim 16 wherein R is hydrogen; R4 is hydrogen; R3 and R6 are both methyl or R6 is hydrogen and R3 is hydrogen, methyl, trifluoromethyl, methylthio or mercaptomethyl; R5 is hydrogen, acetyl, or benzoyl; and X1-R1 and X2-R2 join to form

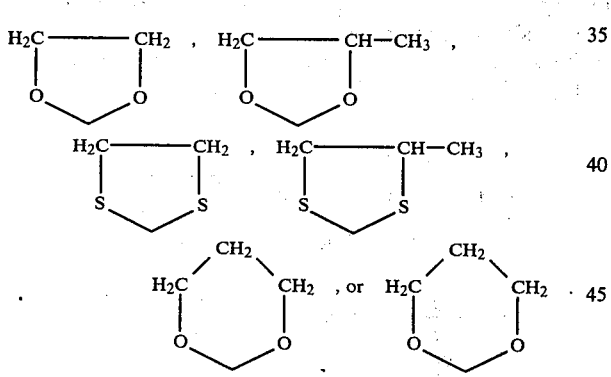

18. The compound of claim 17 wherein R, R4, R5 and R6 are hydrogen, R3 is methyl; and m is one.

19. The compound of claim 18, [7(S),8S]-7-(3-mercapto-2-methyl-1-oxopropyl)-1,4-dioxo-7-azaspiro[4.4-]nonane-8-carboxylic acid.

20. The compound of claim 18, [2(S),3S]-2-(3-mercapto-2-methyl-1-oxopropyl)-6,10-dioxo-2-azaspiro[4.5]decane-3-carboxylic acid.

21. The compound of claim 18, [7(S),8S]-7-(3-mercapto-2-methyl-1-oxopropyl)-7-aza-1,4-dithiaspiro[4.4-]nonane-8-carboxylic acid.

22. The compound of claim 18, [7(S),8S]-7-(3-mercapto-2-methyl-1-oxopropyl)-1,4-dioxo-7-azaspiro[4.4-]nonane-2-methyl-8-carboxylic acid.

23. The compound of claim 17 wherein R, R4,R5 and R6 are hydrogen, R3 is trifluoromethyl; and m is one.

24. The compound of claim 23, (8S)-7-(3-mercapto-2-trifluoromethyl-1-oxopropyl)-1,4-dioxo-7-azaspiro[4.4-]nonane-8-carboxylic acid.

25. The compound of claim 8 wherein R3 and R4 are other than —(CH2)n—SH and R5 is

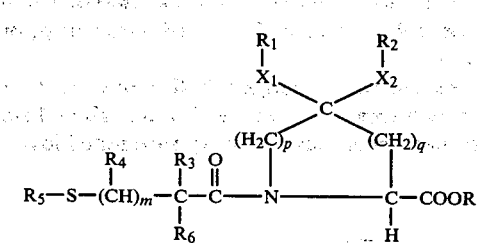

26. The compound of claim 25, (S,S,S,S)-7,7'-[dithiobis(2-methyl-1-oxo-3,1-propanediyl)]-bis[1,4-dioxo-7-azaspiro[4.4]nonane-8-carboxylic acid].

27. A composition for treating hypertension containing a pharmaceutically acceptable carrier and from 10 to 500 mg. of a compound or mixture of compounds or pharmaceutically acceptable salts thereof of the formula

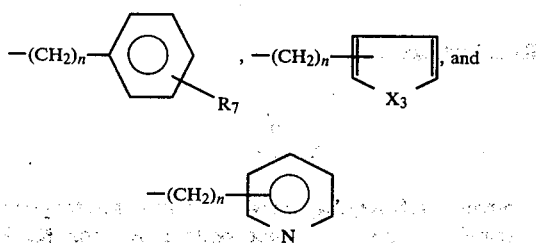

wherein

R is hydrogen or lower alkyl;

R1 and R2 are independently selected from the group consisting of lower alkyl, lower alkenyl, lower alkynyl, cycloalkyl, halo substituted lower alkyl, hydroxy substituted lower alkyl, —(CH2)n—⌬—R7 , —(CH2)n—furyl—X3 , and —(CH2)n—pyridyl , or R1 and R2 join together in a polymethylene chain of the formula

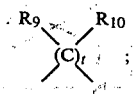

X1, X2 and X3 are independently selected from the group consisting of oxygen and sulfur;

R3 and R4 are independently selected from the group consisting of hydrogen, lower alkyl, lower alkylthio, —(CH2)n—SH, and halo substituted lower alkyl;

R6 is hydrogen or lower alkyl provided that R6 is lower alkyl only when R3 is lower alkyl;

m is zero, one, or two;

n is one, two, or three;

p and q are each one or two provided that both are not two;

t is two or three;

R7 is hydrogen, lower alkyl of 1 to 4 carbons, lower alkoxy of 1 to 4 carbons, lower alkylthio of 1 to 4 carbons, chloro, bromo, fluoro, trifluoromethyl or hydroxy;

R9 and R10 are both hydrogen, both lower alkyl, or one is hydrogen and the other is lower alkyl, halo substituted lower alkyl, hydroxy substituted lower alkyl,

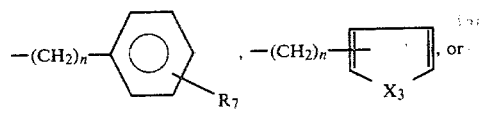

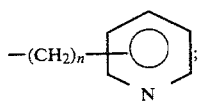

R5 is hydrogen,

or provided that neither R3 nor R4 is —(CH2)n—SH

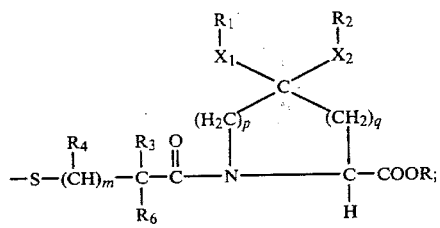

and

R8 is lower alkyl, halo substituted lower alkyl, —(CH2)r-cycloalkyl,

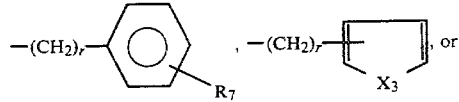

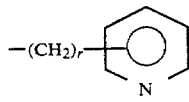

wherein r is zero, one, two, or three and R7 and X3 are as defined above.

28. The method of alleviating hypertension by administering an effective amount of the composition of claim 27.

29. A composition for treating hypertension containing a pharmaceutically acceptable carrier, 15 to 300 mg. of a diuretic selected from the group consisting of chlorthiazide, hydrochlorothiazide, flumethiazide, hydroglumethiazide, benzdoflumethiazide, methchlothiazide, trichlormethiazide, polythiazide, benzthiazide, ethacrynic acid, tricrynafen, chlorthalidone, furosemide, musolimine, bumetanide, triamterene, amiloride, spironolactone and pharmaceutically acceptable salts thereof, and 30 to 600 mg. of a compound or mixture of compounds or pharmaceutically acceptable salts thereof of the formula

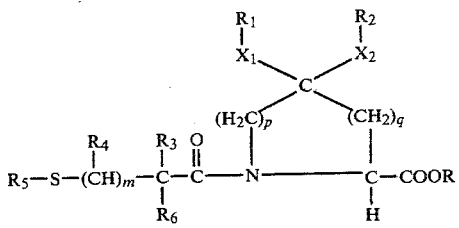

wherein
R is hydrogen or lower alkyl;
R1 and R2 are independently selected from the group consisting of lower alkyl, lower alkenyl, lower alkynyl, cycloalkyl, halo substituted lower alkyl, hydroxy substituted lower alkyl,

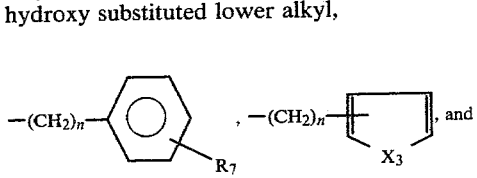

or R1 and R2 join together in a polymethylene chain of the formula

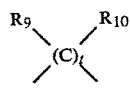

$X_1$, $X_2$ and $X_3$ are independently selected from the group consisting of oxygen and sulfur;

R3 and R4 are independently selected from the group consisting of hydrogen, lower alkyl, lower alkylthio, —(CH2)n—SH, and halo substituted lower alkyl;

R6 is hydrogen or lower alkyl provided that R6 is lower alkyl only when R3 is lower alkyl;

m is zero, one or two;
n is one, two, or three;
p and q are each one or two provided that both are not two;
t is two or three;
R7 is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;
R9 and R10 are both hydrogen, both lower alkyl, or one is hydrogen and the other is lower alkyl, halo substituted lower alkyl, hydroxy substituted lower alkyl,

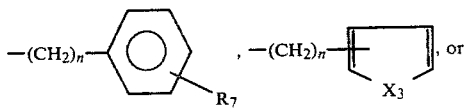

-continued
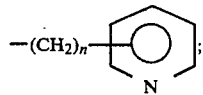
$R_5$ is hydrogen,
or provided that neither $R_3$ nor $R_4$ is $-(CH_2)_n-SH$
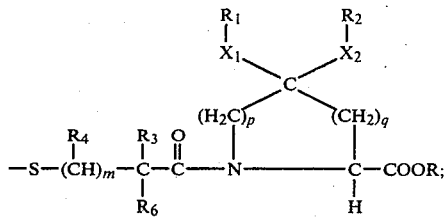
and
$R_8$ is lower alkyl, halo substituted lower alkyl,
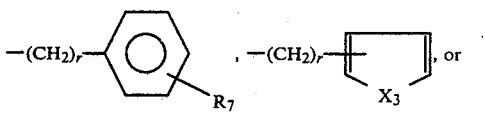
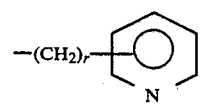
wherein r is zero, one, two or three and $R_7$ and $X_3$ are as defined above.
30. The method of alleviating hypertension by administering an effective amount of the composition of claim 29.
* * * * *

UNITED STATES PATENT AND TRADEMARK OFFICE
CERTIFICATE OF CORRECTION

PATENT NO. : 4,311,697

DATED : January 19, 1982

INVENTOR(S) : John Krapcho

It is certified that error appears in the above-identified patent and that said Letters Patent is hereby corrected as shown below:

Column 10, line 63, delete "/3-". Column 20, line 50, "2-pipecolic acid bor the N-carbobenzyloxy-4-keto-" should read -- 2-pipecolic acid for the N-carbobenzyloxy-4-keto- --.

Col. 26, line 20, "[4.]" should be -- [4.4] --.
Col. 27, line 32, "thylprpionyl" should be -- thylpropionyl --.
Col. 27, line 41, "hy)" should be -- y) --.
Col. 29, line 42, delete "B". Col. 35, Example 60, the right hand portion of the first formula should be --  -- . Col. 40, Example 82, under $R_8$ the formula should read --  -- . Col. 46, line 14

"-7-mercapto-" should be -- -7-(3-mercapto- --.
Col. 46, line 27, "aricel" should be -- Avicel -- .

Signed and Sealed this

Fourteenth Day of February 1984

[SEAL]

Attest:

GERALD J. MOSSINGHOFF

Attesting Officer

Commissioner of Patents and Trademarks